(12) United States Patent
Nilsson et al.

(10) Patent No.: US 8,425,229 B2
(45) Date of Patent: Apr. 23, 2013

(54) METHOD AND SYSTEM FOR DENTAL PLANNING

(75) Inventors: Urban Nilsson, Hålta (SE); Matts Andersson, Lerum (SE)

(73) Assignee: Nobel Biocare Services AG, Glattbrugg (CH)

( * ) Notice: Subject to any disclaimer, the term of this patent is extended or adjusted under 35 U.S.C. 154(b) by 257 days.

(21) Appl. No.: 12/600,633

(22) PCT Filed: May 21, 2008

(86) PCT No.: PCT/EP2008/004072
§ 371 (c)(1), (2), (4) Date: Nov. 17, 2009

(87) PCT Pub. No.: WO2008/145293
PCT Pub. Date: Dec. 4, 2008

(65) Prior Publication Data
US 2010/0151417 A1    Jun. 17, 2010

(30) Foreign Application Priority Data
May 25, 2007    (SE) ........................................ 0701296

(51) Int. Cl.
*A61C 13/00* (2006.01)
(52) U.S. Cl.
USPC .......................................... 433/172; 433/213
(58) Field of Classification Search .................. 433/172, 433/213, 214, 223
See application file for complete search history.

(56) References Cited

U.S. PATENT DOCUMENTS

| | | | |
|---|---|---|---|
| 4,836,778 A | | 6/1989 | Baumrind et al. |
| 5,052,928 A | * | 10/1991 | Andersson .................... 433/172 |
| 5,059,758 A | | 10/1991 | Andersson |
| 5,069,622 A | | 12/1991 | Rangert et al. |
| 5,192,173 A | | 3/1993 | Andersson et al. |
| 5,192,472 A | | 3/1993 | Andersson |
| 5,440,496 A | | 8/1995 | Andersson et al. |
| 5,497,336 A | | 3/1996 | Andersson et al. |
| 5,565,152 A | | 10/1996 | Odén et al. |
| 5,587,912 A | | 12/1996 | Andersson et al. |
| 5,607,305 A | | 3/1997 | Andersson et al. |
| 5,652,709 A | | 7/1997 | Andersson et al. |

(Continued)

FOREIGN PATENT DOCUMENTS
WO    WO 98/20807    5/1998

OTHER PUBLICATIONS

Declaration of Non-establishment of International Search Report for International Application No. PCT/EP2008/004072, mailed on Oct. 7, 2008, in 2 pages.

*Primary Examiner* — Ralph Lewis
(74) *Attorney, Agent, or Firm* — Knobbe, Martens, Olson & Bear, LLP.

(57) ABSTRACT

Methods are provided for computer-based planning of a dental restorative procedure of a patient having a craniooral space and/or of at least one dental component for the dental restorative procedure. Certain methods include determining a first spatial position of a first boundary surface, in the craniooral space, of a first dental unit of a dental restoration; determining a second spatial position of a second boundary surface, in the craniooral space remote the first boundary surface, of a second dental unit of the dental restoration; and determining a third spatial position of at least a portion of the at least one dental component relative at least one of the first and second spatial positions.

19 Claims, 24 Drawing Sheets

U.S. PATENT DOCUMENTS

| | | | |
|---|---|---|---|
| 5,725,376 A * | 3/1998 | Poirier | 433/172 |
| 5,733,126 A | 3/1998 | Andersson et al. | |
| 5,752,828 A | 5/1998 | Andersson et al. | |
| 5,800,174 A | 9/1998 | Andersson | |
| 5,851,115 A | 12/1998 | Carlsson et al. | |
| 5,880,962 A | 3/1999 | Andersson et al. | |
| 5,938,446 A * | 8/1999 | Andersson et al. | 433/223 |
| 6,015,289 A | 1/2000 | Andreiko et al. | |
| 6,049,743 A | 4/2000 | Baba | |
| 6,062,861 A | 5/2000 | Andersson | |
| 6,068,482 A | 5/2000 | Snow | |
| 6,099,314 A | 8/2000 | Kopelman et al. | |
| 6,152,731 A | 11/2000 | Jordan et al. | |
| 6,212,442 B1 | 4/2001 | Andersson et al. | |
| 6,322,359 B1 | 11/2001 | Jordan et al. | |
| 6,607,386 B1 | 8/2003 | Andersson et al. | |
| 6,726,478 B1 | 4/2004 | Isiderio et al. | |
| 6,821,123 B2 | 11/2004 | Andersson et al. | |
| 6,979,196 B2 | 12/2005 | Nikolskiy et al. | |
| 7,089,070 B1 | 8/2006 | Andersson et al. | |
| 7,112,065 B2 | 9/2006 | Kopelman et al. | |
| 7,175,435 B2 | 2/2007 | Andersson et al. | |
| 7,220,124 B2 | 5/2007 | Taub et al. | |
| 7,286,954 B2 | 10/2007 | Kopelman et al. | |
| 7,333,874 B2 * | 2/2008 | Taub et al. | 700/117 |
| 7,347,688 B2 | 3/2008 | Kopelman et al. | |
| 7,347,690 B2 | 3/2008 | Jordan et al. | |
| 7,354,270 B2 | 4/2008 | Abolfathi et al. | |
| 7,357,634 B2 | 4/2008 | Knopp | |
| 7,363,239 B1 | 4/2008 | Andersson et al. | |
| 7,435,088 B2 | 10/2008 | Brajnovic | |
| 7,488,174 B2 | 2/2009 | Kopelman et al. | |
| 2004/0063062 A1 | 4/2004 | Brajnovic | |
| 2004/0224286 A1 | 11/2004 | Kaza et al. | |
| 2005/0136371 A1 | 6/2005 | Abolfathi et al. | |
| 2005/0277091 A1 | 12/2005 | Andersson et al. | |
| 2006/0212260 A1 | 9/2006 | Kopelman et al. | |
| 2006/0275737 A1 | 12/2006 | Kopelman et al. | |
| 2007/0077537 A1 | 4/2007 | Taub et al. | |
| 2007/0154867 A1 | 7/2007 | Taub et al. | |
| 2007/0203663 A1 | 8/2007 | Kopelman et al. | |
| 2007/0238066 A1 | 10/2007 | Kopelman et al. | |
| 2007/0281284 A1 | 12/2007 | Andersson et al. | |
| 2008/0038688 A1 | 2/2008 | Kopelman et al. | |
| 2008/0038692 A1 | 2/2008 | Andersson et al. | |
| 2008/0057466 A1 | 3/2008 | Jordan et al. | |
| 2008/0090211 A1 | 4/2008 | Andersson | |
| 2008/0193899 A1 | 8/2008 | Karlsson et al. | |
| 2008/0241796 A1 | 10/2008 | Ce et al. | |
| 2008/0259411 A1 | 10/2008 | Karlsson | |
| 2009/0026643 A1 * | 1/2009 | Wiest et al. | 264/16 |
| 2009/0123887 A1 | 5/2009 | Brajnovic | |
| 2009/0274993 A1 | 11/2009 | Bergstrom et al. | |

* cited by examiner

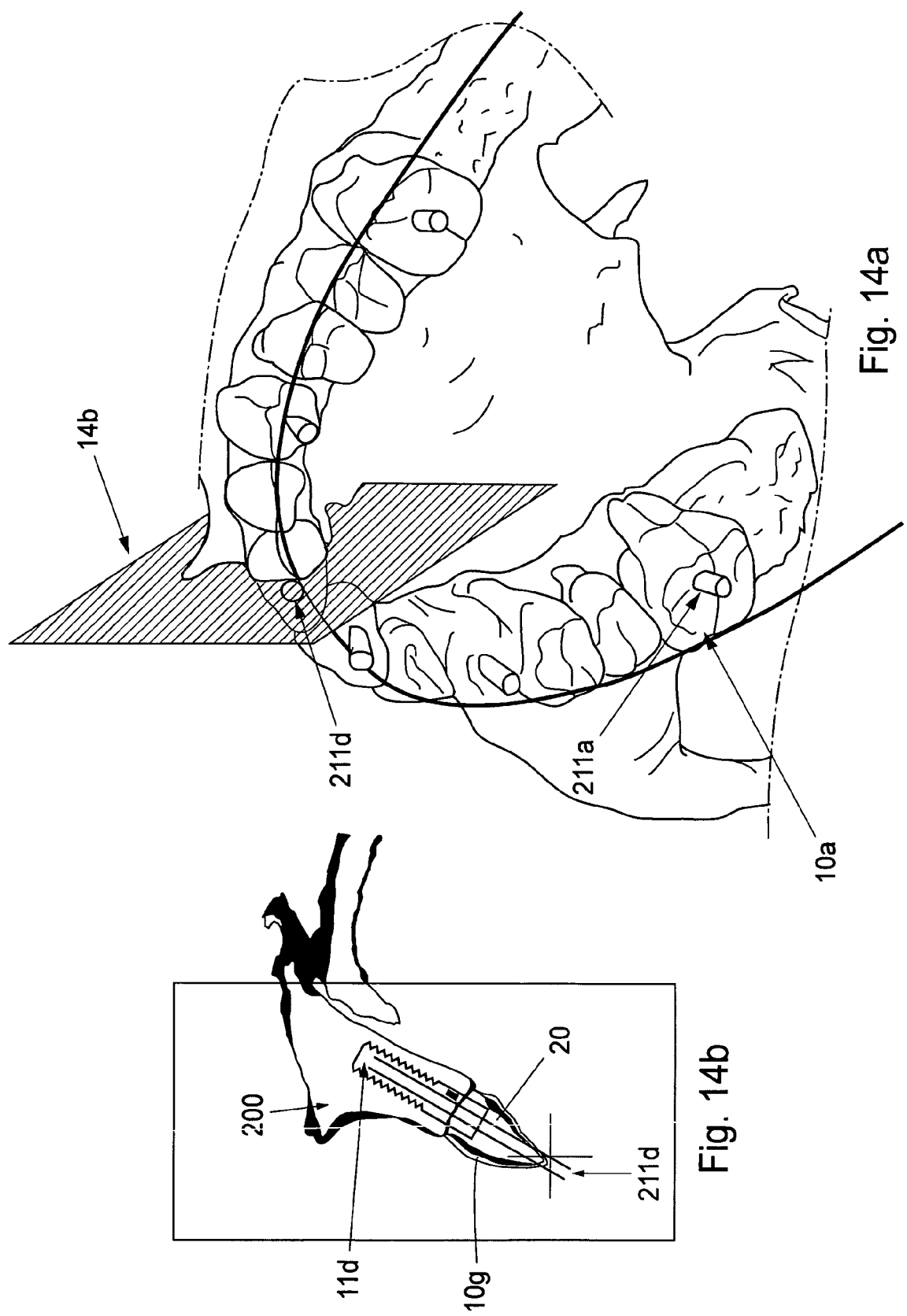

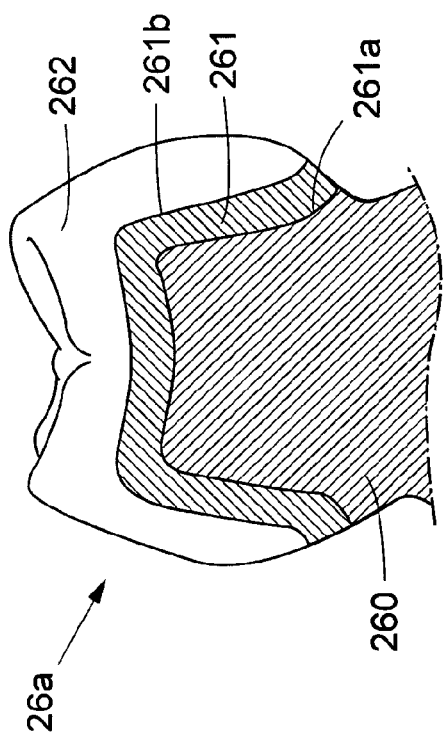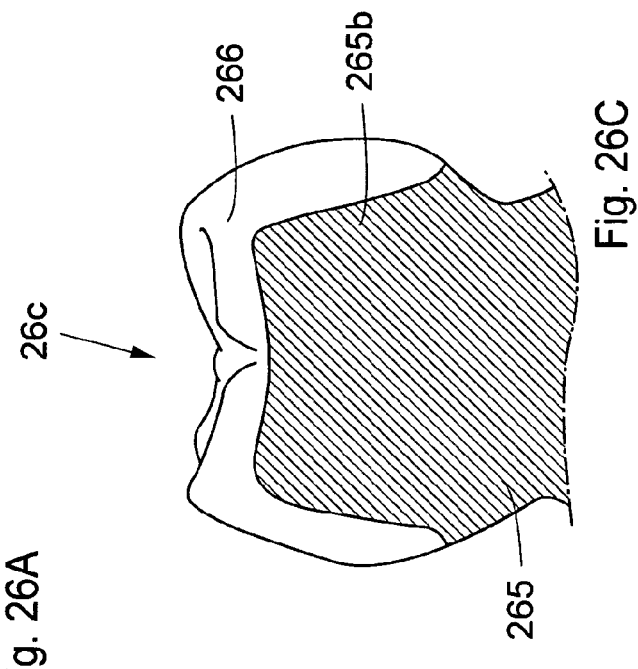

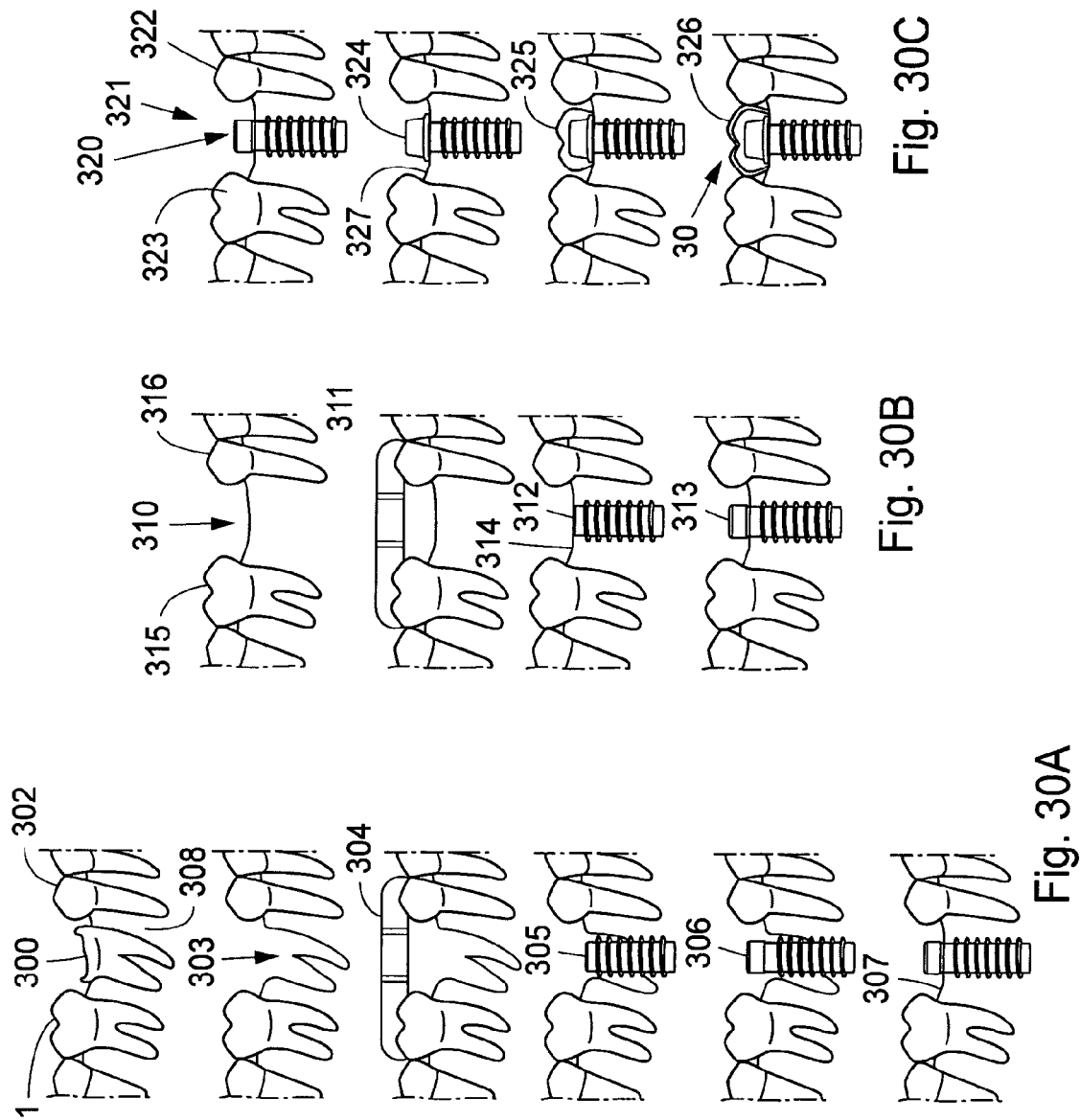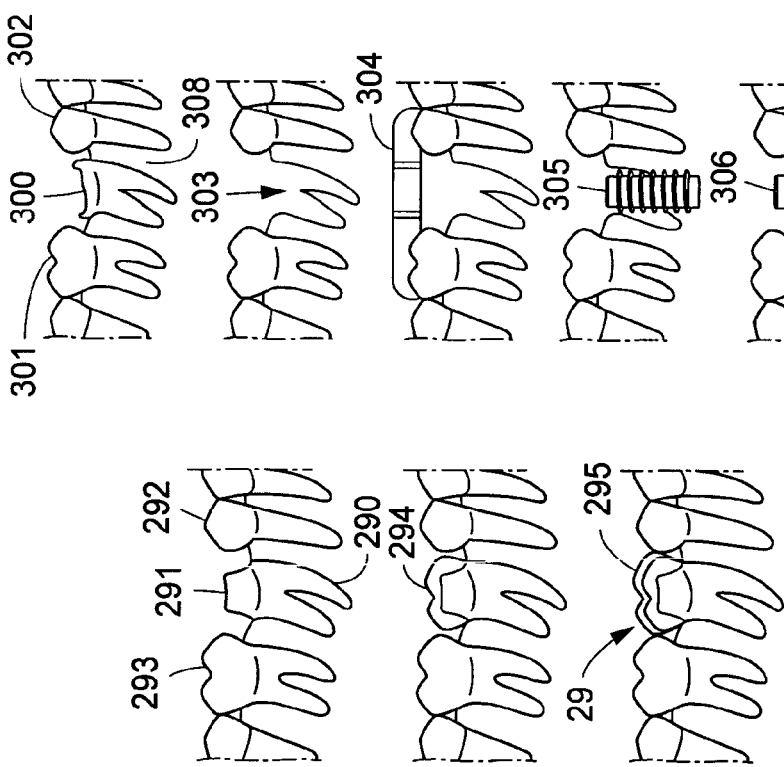
Fig. 29
Fig. 30A
Fig. 30B
Fig. 30C

METHOD AND SYSTEM FOR DENTAL PLANNING

CROSS-REFERENCE TO RELATED APPLICATIONS

This application is a national stage application under 35 U.S.C. §371 of PCT Application No. PCT/EP2008/004072, filed on May 21, 2008, which published in English as WO 2008/145293 A2 on Dec. 4, 8008 and which claims priority benefit of Swedish Patent Application No. 0701296-6, filed on May 25, 2007, the entire contents of which applications and publication are herein incorporated by reference in their entirety.

BACKGROUND

This application pertains in general to the field of dentistry. More particularly the invention relates to a method and system for planning of dental restorative procedures and for producing dental restorations and/or dental components related to the dental restorative procedures.

Dental implant and dental restoration planning has been based on expertise and experience of a skilled dentist and was hitherto a manual task. Although it is known to perform the planning in a software based computer environment, visualizing virtual cranial and dental models, the planning has been made manually by the dentist. Based on this manual planning, dental restorations and related products thereto, such as drill guides were produced. Such a system is for instance disclosed in the international publications WO02/053056 and WO2005/055856 of the same applicant as the present application. However, these systems are dependent on the human factor and an imperfect planning may not be detected by the software based planning system.

Hence, an improved system for planning dental restorative procedure of a patient and/or of planning at least one dental component for said dental restorative procedure, capable of reducing the effect of the human factor, would be advantageous.

SUMMARY

Accordingly, embodiments of the present invention preferably seek to mitigate, alleviate or eliminate one or more deficiencies, disadvantages or issues in the art, such as the above-identified, singly or in any combination by providing a method, a system, a computer program product, a computer-readable medium, a medical workstation, and a graphical interface useful for planning a dental restorative procedure of a patient and/for planning at least one dental restoration and/or product related to the dental restorative procedure.

Certain different aspects of the invention are recited in the attached patent claims.

According to one aspect of the invention, a method is provided, wherein the method is useful for computer-based planning of a dental restorative procedure of a patient having a craniooral space, and/or of at least one dental component for the dental restorative procedure. The method comprises determining a first spatial position of a first boundary surface, in the craniooral space, of a first dental unit of a dental restoration; determining a second spatial position of a second boundary surface, in the craniooral space remote the first boundary surface, of a second dental unit of the dental restoration; and determining a third spatial position, of at least a portion of the at least one dental component, relative at least one of the first and second spatial positions. According to a second aspect of the invention, a system that is useful for computer-based planning of a dental restorative procedure of a patient having a craniooral space, and/or of at least one dental component for the dental restorative procedure, is provided. The system comprises a first unit for determining a first spatial position of a first boundary surface, in the craniooral space, of a first dental unit of a dental restoration; a second unit for determining a second spatial position of a second boundary surface, in the craniooral space remote the first boundary surface, of a second dental unit of the dental restoration; and a third unit for determining a third spatial position, of at least a portion of the dental component, relative at least one of the first and second spatial positions. According to a third aspect of the invention, a computer program for processing by a computer is provided. The computer program computer program is useful for computer-based planning of a dental restorative procedure of a patient having a craniooral space, and/or of at least one dental component for the dental restorative procedure. The computer program comprises a first code segment for determining a first spatial position of a first boundary-surface, in the craniooral space, of a first dental unit of a dental restoration; a second code segment for determining a second spatial position of a second boundary surface, in the craniooral space remote the first boundary surface, of a second dental unit of the dental restoration; and a third code segment for determining a third spatial position, of at least a portion of the dental component, relative at least one of the first and second spatial positions. The computer program may be embodied on a computer-readable medium.

According to yet a further aspect of the invention, a graphical user interface for dental planning is provided. The graphical user interface comprises components for visualizing the method according to said first aspect of the invention.

According to yet a further aspect of the invention, a medical workstation for carrying out the method of the above mentioned aspect of the invention by running the computer program of the above mentioned further aspect of the invention is provided. The medical workstation may implement the graphical user interface of the above mentioned further aspect of the invention.

Certain further embodiments of the invention are defined in the dependent claims, wherein features for the second and subsequent aspects of the invention are as for the first aspect mutatis mutandis.

Some embodiments of the invention provide automatically adapting a shape of a bridge framework, the shape of a dental veneering, and thus even a bridge structure, e.g., a bridge framework with veneering, as well as a position of a dental implant.

Some embodiments provide for presurgical planning of a dental restorative procedure and production of dental restorations and/or products related to said dental restorative procedure without the need of preparing a plaster model of the patient oral cavity, or CT scanning a prosthesis for providing patient data for planning a dental restorative procedure. Some embodiments of the invention provide for virtual planning of a dental restoration without the need for any-kind of physical patient model.

Some embodiments of the invention provide for a faster and/or more reliable planning of a dental restorative procedure and products used therefor, as manual planning and production work is avoided entirely or to a large extent.

Some embodiments of the invention provide for a reduced possibility of errors during planning of a dental restorative procedure and products used therefor, as an entirely computer based planning is provided.

Some embodiments of the invention provide for entirely virtually computer based suggestion of a dental restorative procedure of a patient having a craniooral space, and/or of at least one dental component for said dental restorative procedure.

Some embodiments of the invention provide for entirely automatically suggestion of a dental restorative procedure of a patient having a craniooral space, and/or of at least one dental component for said dental restorative procedure, wherein said suggestion is based on patient data of the craniooral space.

Some embodiments of the invention provide for a reduced number of transfer steps during production of products used for dental restorative procedures, as only raw patient data has to be input and the rest of the planning method may be performed entirely virtually.

Some embodiments of the invention provide for a flexible planning of a dental restorative procedure and products used therefor, as user input for virtual manipulations or a user accept of automatic placement of virtual dental restorations advance of final placement may be provided.

Some embodiments of the invention provide for an early diagnosis of the dental situation of the patient during planning of a dental restorative procedure and products used therefor.

Some embodiments of the invention provide for a guided dental surgery with reduced inconvenience and pain for the patient, as an optimal fit of a dental restoration is provided. For instance, by virtually planning a final dental restoration without the need of re-scanning the patient with a prosthesis, the number of treatment occasions and total treatment time may be reduced. Furthermore, both final dental restorations and related products, such as drill guides may be provided from the same input data in a single automated procedure.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which In FIG. 1 is a flow chart of an embodiment of a method for virtually planning a dental restoration;

FIG. 14a is a schematic illustration in a view from below of the maxilla bone showing the calculated occlusion line, the position and direction of implants, and a twelve unit implant bridge framework on the six implants, as well as the automatically aligned standard teeth, providing planning of a bridge structure of the bridge framework and applied veneering;

FIG. 14b is a cross sectional view through the plane 14b shown in FIG. 14a, at tooth pos. 21 with an overlayed implant, and the bridge structure comprising the bridge framework and veneering, wherein the boundary surfaces interfacing between these units are shown;

FIGS. 26A-26C are cross sectional views illustrating a morphing technique for improving a dental restoration;

FIG. 29 is a schematic illustration of a virtually-planned dental restoration based on a preparation of an existing tooth of a patient;

FIGS. 30A-30C are schematic illustrations of implantation of a dental implant in jaw bone tissue upon extraction of a tooth, implantation of a dental implant in healed jaw bone tissue at the position of an extracted tooth, and virtual planning of a dental restoration based on an existing dental implant, respectively;

DETAILED DESCRIPTION

Figure 1:
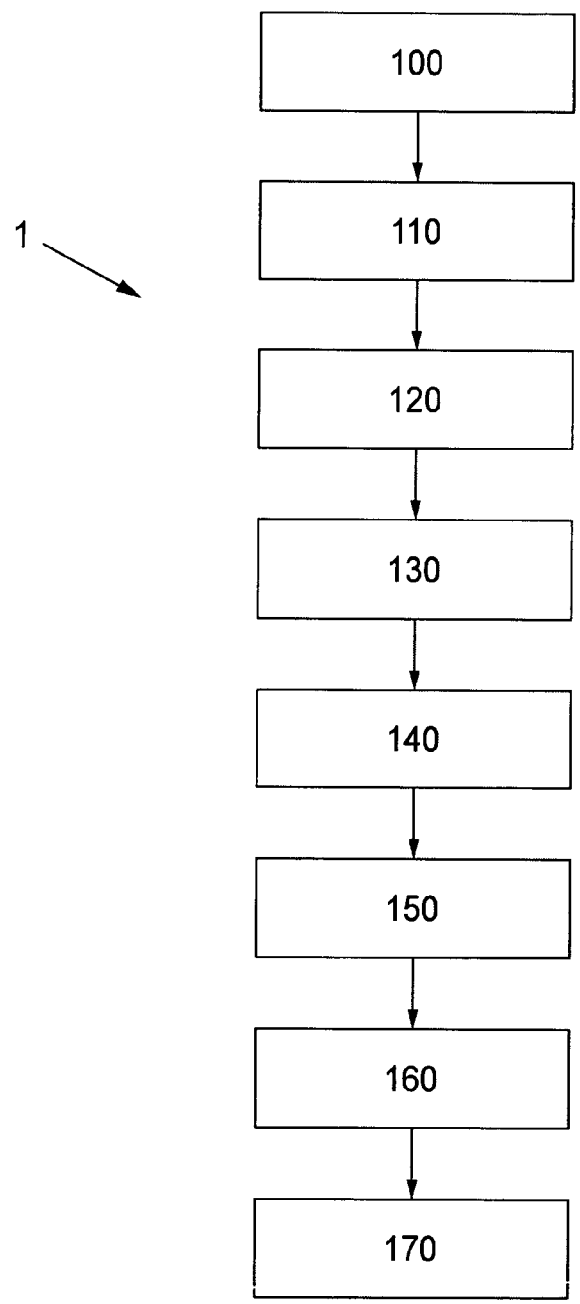

Specific embodiments of the invention now will be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The following description focuses on an embodiment of the present invention applicable to a dental restoration comprising a bridge framework and in particular to a dental implant, and bridge structure comprising a bridge framework dental a veneering construction, planned in the maxilla (upper jaw bone). However, it will be appreciated that the invention is not limited to this application but may be applied to many other dental restorations, including for example single implants with or without a spacer and attached crowns, and may be used in relation to other implant positions, e.g., in the mandibula (lower jaw bone).

A "dental restoration" comprises dental units such as a dental implant, a bridge framework, a bridge structure, a coping, an abutment, a crown, a veneering, a prepared existing tooth for receiving a coping, etc.

A "dental component" comprises one or several units of a dental restoration, and in addition components used during installation of at least parts of a dental restoration, such as surgical templates.

A "craniooral space" comprises the oral cavity and adjacent soft tissue and bone tissue into which a dental restoration is to be installed.

In FIG. 1 a flow chart is given for the purpose of illustrating an embodiment of an improved method of planning a dental restorative procedure and production of dental restorations and/or related products to the dental restorative procedure, as well as automatic or semi automatic preparation of data therefor. The method 1 may comprise the following steps:

100 Acquire patient data;
110 Determine anatomically fixed reference points from acquired patient data;
120 Perform dental planning, based on determined anatomically fixed reference points;
130 Calculate position and orientation of implant(s);
140 Automatic adaptation of an implant bridge framework;
150 Approximation of the final restoration;
160 Surgical template production; and
170 Dental restoration production.

The implant and dental restoration may then be installed in the patient in a per-se known manner by a dentist.

A number of embodiments of the above outlined method will now be elucidated in more detail with reference to FIGS. 2 to 30.

In an embodiment a dental restoration for an edentulous patient and a dental restorative procedure, as well as corresponding products, are virtually planned, which is now described in detail.

100 Acquire Patient Data

Patient data to be used in the subsequent virtual dental planning method may be acquired in various ways.

The craniooral space of a patient may be scanned by various data generating modalities or apparatuses. For instance, a dental impression of the patient's oral cavity or a part thereof may be produced. Imaging methods, like CT and MR or X-ray, may be used to provide data on deeper anatomical regions of the patient that are not obtainable by surface based data acquiring techniques. Probes may be used to map the soft tissue in the oral cavity of a patient. In addition, data from several input sources may be combined or merged in order to provide patient data serving as input data to the subsequent dental planning method.

A dental impression is often used to create an imprint or negative likeness of for instance the teeth and adjacent portions of the jaw, such as tooth formations, the contour of the gums, etc. Also, for edentulous patients, an impression of only the gums may be taken. The impression is made preparatory to dental repair or restoration of missing dental structures. The dental impression provides data for the topography of an oral cavity of a patient. The dental impression may directly be scanned by means of a three dimensional (3D) scanner system. Patient data may also be acquired from 3D scanning a plaster model produced from such a dental impression. Other methods of acquiring patient data comprise MR scanning the craniooral space of the patient; intra orally 3D surface scanning; using surface probes to determine a thickness of soft tissue in the oral cavity; etc.

As mentioned above, acquired patient data from several different input sources may be matched to provide a combined patient data. Data acquisition and matching methods and systems for planning dental restorations and production of these and related products are detailed described in the co-pending patent application PCT/EP2007/050426 of the same applicant as the present application, filed on Jan. 17, 2007, which hereby is incorporated herein by reference in its entirety.

Sometimes it is not possible to directly acquire an occlusion line of a patient, e.g., for edentulous patients a bite index for acquiring the occlusion line cannot be provided. However, for embodiments of the present method and system this is not necessary. The occlusion line may be reconstructed from anatomically fixed reference points, which are identified in the acquired patient data.

Figure 2:
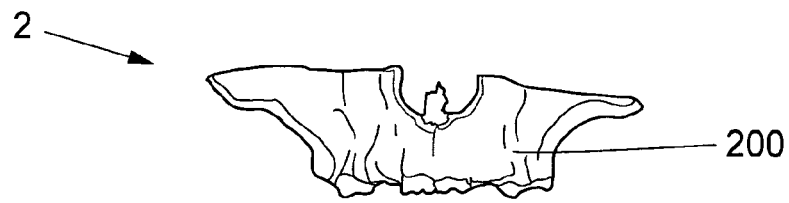
FIGS. 2, 3, and 4 are schematic illustrations of an example of a visualization of an edentulous maxilla bone based on patient data acquired by CT scanning, in a frontal view, lateral view, and view from below, respectively.
Figure 3:
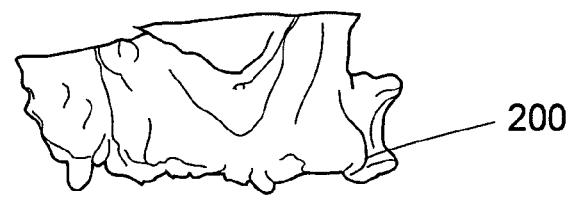
Figure 4:
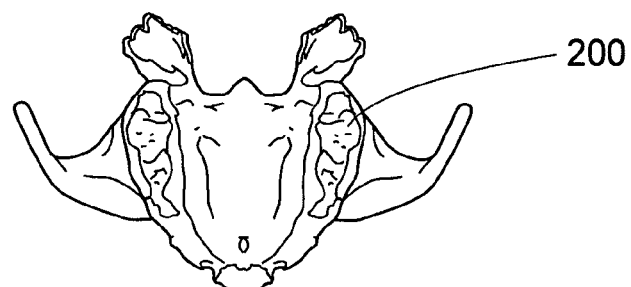
Figure 4A:
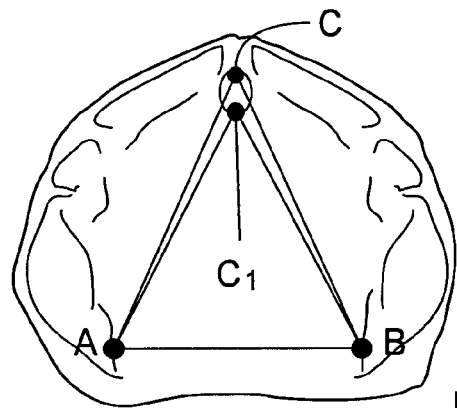
FIGS. 4A-4H are schematic illustrations used for explaining a method according to Staub of positioning teeth based on anatomically fixed reference points.

FIGS. 2, 3 and 4 are schematic illustrations of an example of a visualization of an edentulous maxilla bone 200 based on patient data acquired by CT scanning, in a frontal view, lateral view, and view from below, respectively. In an embodiment, the CT scan data of the maxilla bone is imported into in a computer based software, such as the Procera® software.

110 Determine Anatomically Fixed Reference Points from Acquired Data

In step 110 of the method, the dental planning is in one embodiment started with the determination of anatomically fixed reference points. Starting from these anatomically fixed reference points, an advantageous position of one or more teeth along the dental arch is determined based on defined mathematical relations of the teeth in relation to the anatomically fixed reference points. For instance, a natural position of the canine (front corner) teeth is determined along the dental arch of a jaw. Each of the canine teeth is delimited by the masticating (chewing) surface along the occlusion line in the oral cavity, respectively. That means the actual position of certain teeth, here the canines, is virtually determined in the dental space in the oral cavity. In this manner, a first boundary surface of each of the teeth is determined, namely the boundary surface of a tooth at a defined spatial position along the occlusion line. A surface that has defined spatial position has a defined position in space. From this first boundary surface, having a spatial position, the spatial positions of boundary surfaces of remaining components of a dental restoration of these teeth are virtually determinable. The dental space between the canines may be automatically filled with template front teeth from a teeth library. The teeth library is for instance provided in digital form in a database comprising at least one three-dimensional virtual template tooth object for each tooth in the maxilla and the mandible.

In a similar way, the position of certain molars (posterior teeth) is determinable. The interspaces between teeth at determined positions are automatically filled with further teeth, e.g., template teeth from the teeth library. This will be elucidated further below with reference to steps 120 to 140 of the method.

Figure 5:
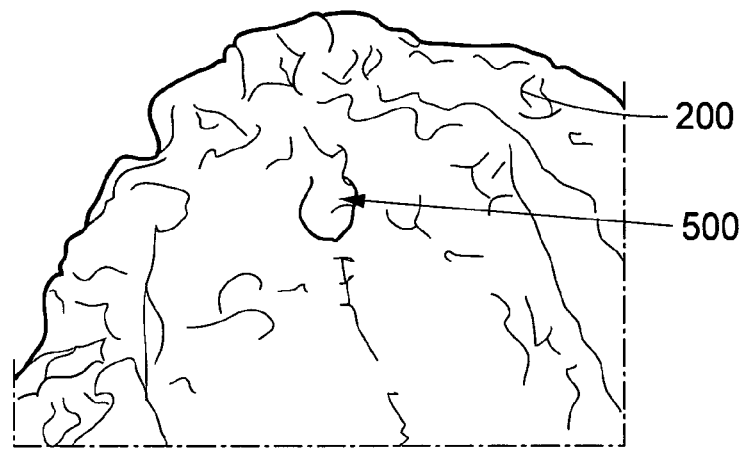
FIG. 5 is a schematic illustration in a view from below of the edentulous maxilla bone showing the incisive canal.
Figure 6:
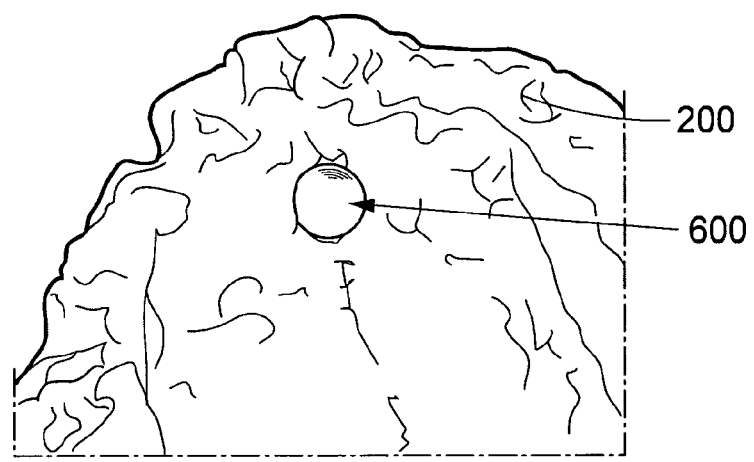
FIG. 6 is a schematic illustration in a view from below of the edentulous maxilla bone showing the incisive canal marked with a first marker.

Nearest below, the determining of anatomically fixed reference points from acquired data is described. FIG. 5 is a schematic illustration in a view from below of the edentulous maxilla bone 200 showing the incisive canal. The virtual model of the maxilla bone 200 is for instance based on acquired CT data. FIG. 6 is a schematic illustration in a view from below of the edentulous maxilla bone 200 showing the incisive canal 500 marked with a first marker 600. The first marker 600 is useful for defining a first anatomically fixed reference point and may be detected automatically by suitable detection algorithms, e.g., based on geometrical shape detection, surface identification. Alternatively, these anatomically fixed reference points may be manually identified and marked as those.

After marking the first anatomically fixed reference point, further anatomically fixed reference points are marked. This is illustrated in FIGS. 7 and 8.

Figure 7:
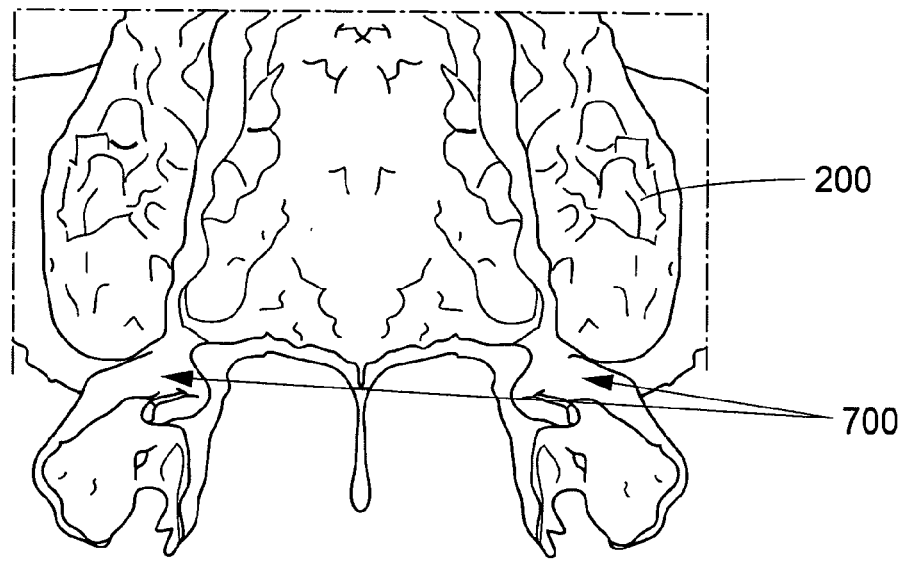
FIG. 7 is a schematic illustration in a view from below of the edentulous maxilla bone showing the pterygoids.
Figure 8:
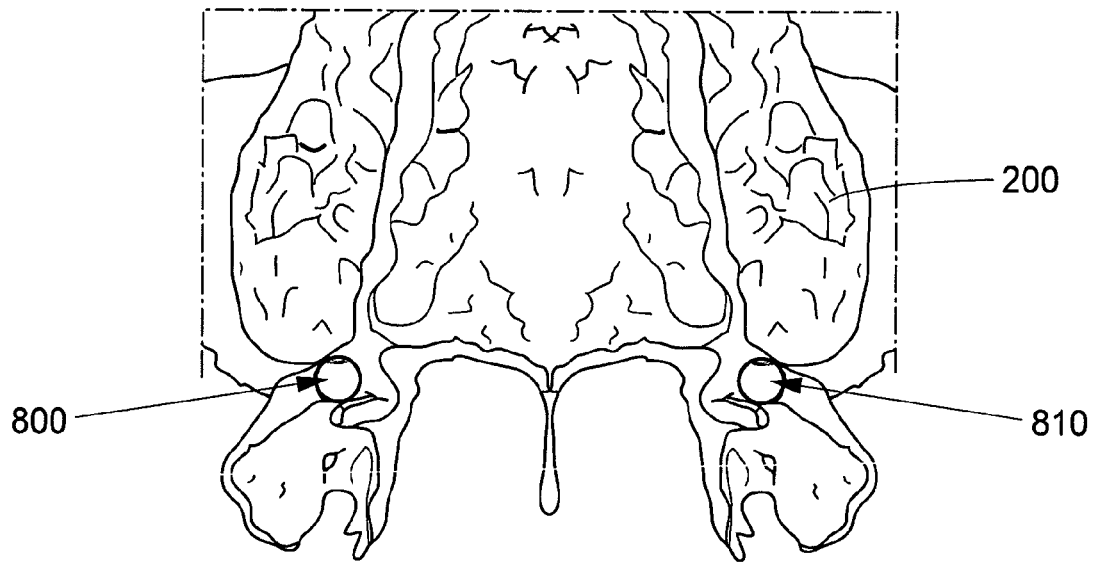
FIG. 8 is a schematic illustration in a view from below of the edentulous maxilla bone showing the pterygoids marked with a second marker and a third marker, respectively.

FIG. 7 is a schematic illustration in a view from below of the edentulous maxilla bone 200 showing the left and right pterygoids 700, as acquired from a CT scan. FIG. 8 is a schematic illustration in a view from below of the edentulous maxilla bone 200 of FIG. 7, showing the pterygoids 700 marked with a second marker 800 and a third marker 810, respectively. The first marker 600, the second marker 800, and the third marker 810 are useful for defining a position of at least one tooth without the need of having information of the position of a pre-existing anatomically natural tooth in the region of that position.

Further anatomically fixed reference points may be detected automatically or marked manually in a similar way. However, three points are sufficient to define a plane in space and to automatically plan the position and direction of at least one of the teeth in relation to the plane.

Figure 9:
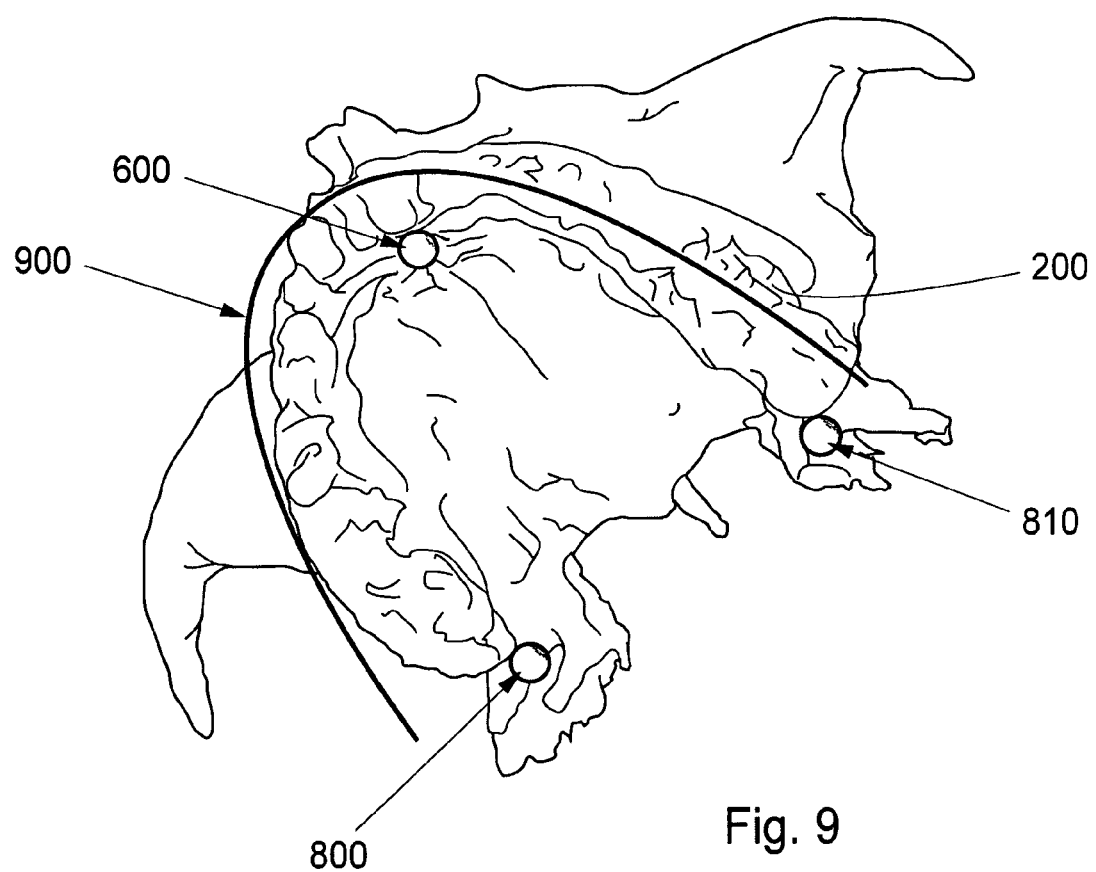
FIG. 9 is a schematic illustration in a view from below of the edentulous maxilla bone showing the first, second and third markers, as well as a calculated occlusion line.

From the three anatomically fixed positions marked by the first, second and third marker, an occlusion line 900, as shown in FIG. 9, is determined by mathematical calculations. Furthermore, spatial positions of virtual teeth along the dental arch are determined from the anatomically fixed positions. From the position of the teeth and/or the spatial position of the occlusion line, a position of at least one dental implant is determined. Knowing the positions of the teeth at the masticating (chewing) surface, e.g., the occlusion line, and the spatial position of implants, interposed structures are determinable. In this way, for instance bridge frameworks are determined that fit with connection interfaces between boundary surfaces, which have a spatial position, of the implants and veneerings, respectively.

One way of locating the natural position of teeth is known as for instance disclosed in WO98/20807, of Karl Heinz Staub, which is incorporated herein by reference in its entirety. The method is described in more detail in "Das Staub™-Cranial-System—Reliabilität der Messpunkte zur Rekonstruktion der Zahnstellung im zahnlosen Kiefer", Panagiotis Lampropoulos, Freiburg, 2003, which is incorporated herein in its entirety. Points in the oral soft tissue are used as anatomically fixed reference points. By using these anatomically fixed reference points, a position of a single tooth or a plurality of teeth in the upper and/or lower jaw is determinable by mathematical calculations. However, the Staub method is based on dental impressions, plaster castings, and manual measurements on the plaster castings. Furthermore, the manual measurements are based on points in soft tissue, or more precisely corresponding points in dental impression based plaster casts thereof. The manual measurements may then be transferred into software that calculates a position of teeth in dental restorations that is very similar to the natural position in the patient before having lost the teeth. Thereby a good occlusion is achieved by dental restorations produced in accordance with these measurements and mathematical calculations. In this manner, highly accurate and predictable dental restorations may be provided. The anatomically fixed reference points are anatomically stable and present in every patient.

Below an example of determining anatomically fixed reference points of the maxillary is given with reference to FIGS. 4A-4G. A schematic example of a mandibula is shown in FIG. 4H with anatomically fixed reference points and geometrical relationships thereof, which are applicable for teeth position calculations.

The anatomically fixed reference points according to the Staub method are symmetrically arranged in relation to each other. The specific points are referred to as Direction points, Induction points, and the Conclusion line.

Directions points are at the point on the ridge connecting line that exactly determines the change in direction in the curve of the pterygoid hamulus. It has a stable topography and is present on both sides of the maxillary.

Induction points are at the point of intersection of the rear contour of the papilla and the median axis of the maxilla produces the posterior induction point. The anterior induction point is defined as the point of intersection of the anterior contour of the papilla and the median axis of the maxilla. It is the only cranial point which is not anatomically stable.

Like the direction points, the Conclusion line is present on both sides and is anatomical stable. It forms the boundary between mobile and immobile mucosa and determines the change in position in the curve of the mucolabial fold. The conclusion line is at the transition from the concave to the convex form of the mucolabial fold.

Connecting the lines between the two direction points A and B, and the two induction points C and C1, results in two isosceles triangles with the two direction points as the hypotenuse of each. These parameters are used to calculate a penta area, which is defined as the base of the orthocranial occlusion plane. The penta area is used to position the teeth in relation to the maxillary incisal point.

The position of the maxillary incisal point is very important when reconstructing human dentition. Its position is a key importance for phonetics and aesthetics. Together with the exact position of the mandibular incisal point, it enables the vertical dimension of occlusion to be reconstructed to its exact position.

The two isosceles triangles A-B-C and A-B-C1 are determined as described above. The distance from the right canine apex to the left canine apex is determined. Any anatomical conditions of alveolar ridges, palatal fold, etc. do not have an effect on this position. The parameters required for the calculation are topographically stable and enable patient-specific and jaw-specific positioning of the canines.

Figure 4B:
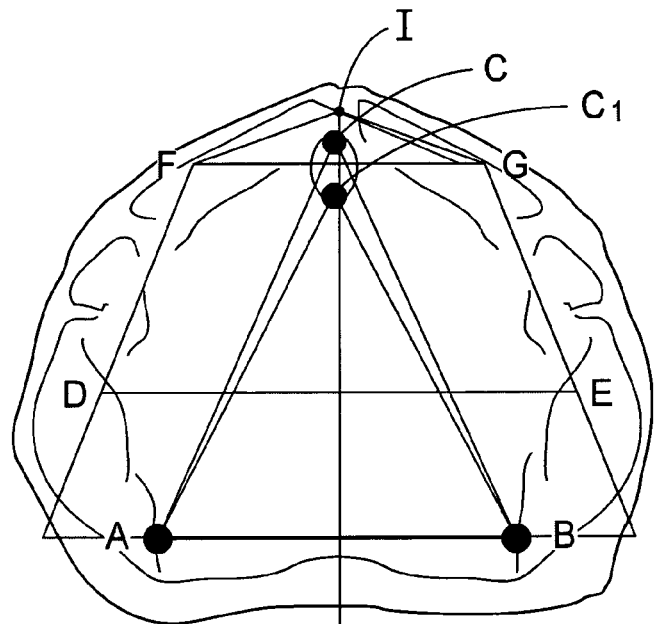
Figure 4C:
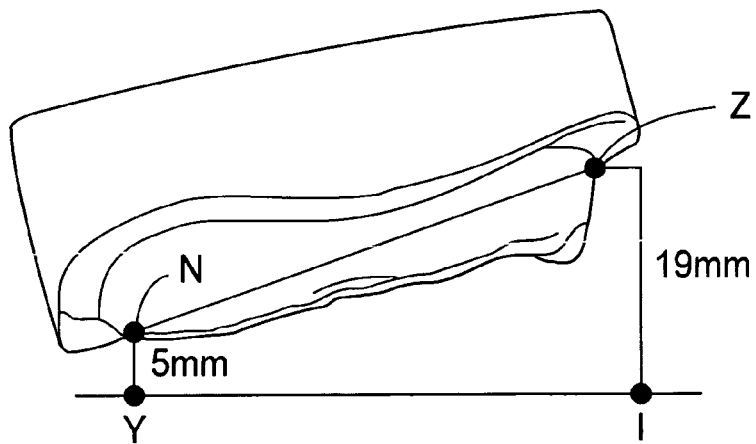
Figure 4D:
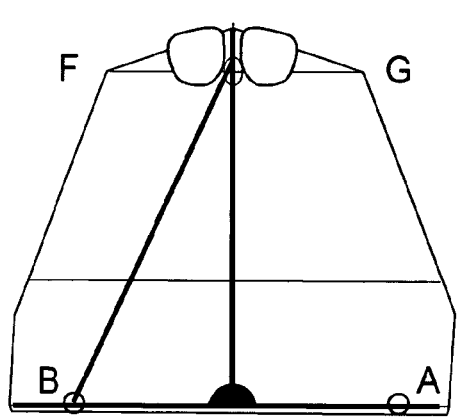

In FIG. 4B the following points are shown: A=right Directional point, B=left Directional point, C1=rear Induction point, C=frontal Induction point, I=Incisal point, F=right canine point, G=left canine point, D=right molar point, E=left molar point, FG=distance between canines, DF=right extension of molars, EG=Left extension of molars, DE=transversal limitation line of the molar extension.

The following points and distances are determined in order to determine the penta area delimited by the points DFIGE in FIG. 4B: the incisal point I, the distance FG of the canines, the distance DE of the molar teeth.

In order to provide a reconstruction of the natural teeth position in the edentulous jaw, the two dimensional position of the incisal point I is determined. For this purpose, the distance BC is swiveled with 90 degrees and positioned in the median axis of the maxilla, whereby the distance NI is obtained. The starting point of the distance NI corresponds to the point of intersection of the median axis with the distance AB, see FIG. 4D. The equation NI=BC is resulting.

Figure 4E:
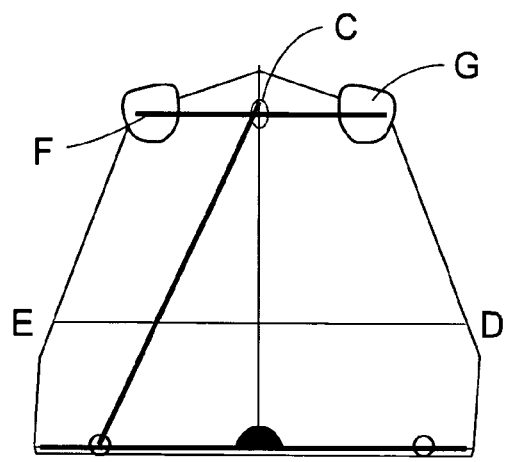
Figure 4F:
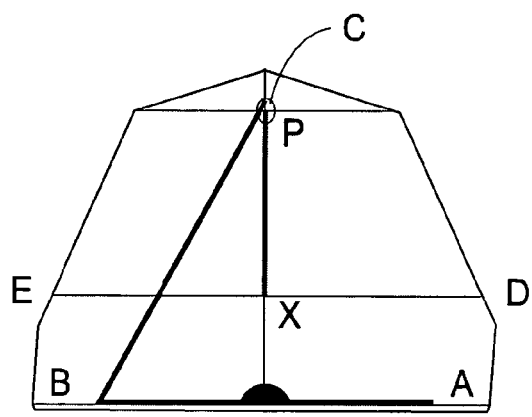
Figure 4G:
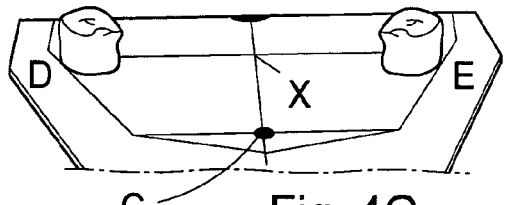
Figure 4H:
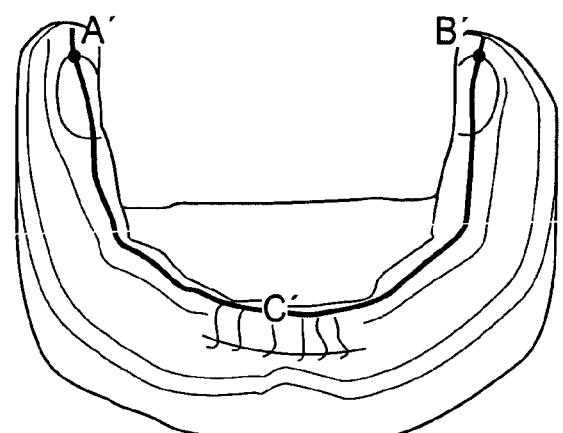

The distance FG between the canines is calculated as follows, see FIG. 4E: FG=2BC/3.

This assumes that FG is parallel to AB and that FG<AB. The distance FG has an extension through the centre of the papilla incisiva.

Now the extension of the molar teeth is calculated. The points D and E are the rear points of the distances FD and GE, respectively. These distances provide the position of the buccal occlusion points of the dental restorations along the molar extensions in the penta area, see FIG. 4B. The distance DE extends perpendicular through the median axis at point X, see FIG. 4F. For calculation of the distance PX the following equation applies: PX=BC×0.55. The transversal limitation line DE of the molar extension results from the sum of the distances XD and XE, wherein the length of these distances is identical, see FIG. 4G.

As [XD=((BC/2)+2 mm)] and DE=2 XD, results: DE=2× (BC/2)+2 mm), e.g., DE=BC+4 mm. Wherein the constant of 2 mm is empirically determined.

The three dimensional relation of the points D, F, I, G, E result in the position of the penta area.

A mathematical constant value is assigned to the penta area in the maxillary and mandibular, respectively. The constant value determines the incisal point in three dimensional space.

The constant is defined as the distance from the conclusion line and amounts to 19 mm in the maxillary and to 17 mm in the mandibular. These values are again empirically determined. In the maxillary, the constant of 19 mm is in correlation to the points N and Z and defines in combination with the mathematically determined penta are the incisal point in space, see FIG. 4C. The distance NY=5 mm corresponds to the distance from the left or right directional point in the maxillary to the opposed mandibular, respectively. The 17 mm constant of the mandibular is defined as the distance from the center of the conclusion line of the mandibular to the incisal point thereof.

As mentioned above, Staub determines direction points, an induction point, and a conclusion line. Directions points A and B correspond to the second marker 800 and the third marker 810 in FIG. 8. An induction point C1 is at the point of intersection of the rear contour of the papilla and the median axis of the maxilla produces the posterior induction point, which corresponds to the lower boundary of the first marker 600 in FIG. 6. Connecting the lines between the two direction points A and B, and the induction point C1 results in an isosceles triangle with the two direction points as the hypotenuse thereof. These parameters are used to virtually calculate the position of the teeth of a dental restoration.

FIG. 9 is a schematic illustration in a view from below of the edentulous maxilla bone 200 showing the first, second and third markers, as well as a calculated occlusion line 900.

Positioning of teeth in the lower jaw may also be done automatically according to similar principles. In FIG. 4H anatomically fixed reference points A', B', and C' are illustrated. From these reference points, a penta area for the mandibular are calculated and teeth are positioned accordingly.

In order to check if the position of the teeth planned in such an automatic manner is correct, the teeth may be positioned in a virtual articulator. If misalignment of teeth is detected in the virtual articulator, the position and direction of concerned teeth may automatically be adjusted.

For example, in case a single tooth restoration is to be planned, the correct occlusion of a tooth positioned according to the above principle may be checked in relation to the other teeth. Data for the remaining teeth is provided in the acquired patient data, e.g., from a CT scan, a dental impression, or combinations of several data sources.

The method according to Staub is based on anatomical points identifiable in the oral soft tissue that are anatomically fixed reference points. Some embodiments of the invention are based on anatomical points identifiable in the bone tissue that are anatomically fixed reference points. When using these bone tissue based anatomically fixed reference points the method according to Staub is still applicable in embodiments. For instance an offset due to the thickness of soft tissue overlaying the bone tissue may be considered in calculations as described above. The offset may be based on actual measurements of the soft tissue thickness or offset at the location of the anatomically fixed reference points in bone tissue. Alternatively, a fixed offset may be used, e.g., based on empirical patient data.

It is pointed out that the method according to Staub for reconstructing positions of teeth is only one of many possible methods applicable within the scope of embodiments of the present invention. For instance chapter 5.2 ("Rekonstruktion von Zahnpositionen") of the above cited publication of Panagiotis Lampropoulos, which specifically is incorporated by reference herein, lists various publications according to which calculations of the position of the occlusion line, and positions of teeth of dental prosthesis may be reconstructed from anatomically fixed points.

One of many alternative methods is for instance to calculate the plane of occlusion from the hamular notches or the temporal bones used by the commercially available product Acculiner™. The hamular notches or the temporal bones are stable landmarks in the cranium defined a so-called HIP plane, by means of which the Acculiner™ three dimensionally determines the occlusion plane.

The occlusion plane may also be determined by means of cepaholometric criteria according to Augsburger R H (1953), Occlusal plane relation to facial type, J Prosthet Dent 3:755-770; L'Estrange P R, Vig P S (1975), A comparative study of the occlusal plane in dentulous and edentulous subjects, J Prosthet Dent 33:495-503; Monteith B D (1985), A cephalometric method to determine the angulation of the occlusal plane in edentulous patients; J Prosthet Dent 54:81-87; Monteith B D (1985), Cephalometrically programmed adjustable plane: a new concept in occlusal plane orientation for complete-denture patients, J Prosthet Dent 54:388-394; Sinobad D (1988), The position of the occlusal plane in dentulous subjects with various skeletal jaw-relationships, J Oral Rehabil 15:489-498; Kollmar U (1990); Möglichkeiten der prothetischen Rehabilitation zahnloser Patienten mit Hilfe des Fernröntgenseitenbildes, ZWR 99:451-457.

Other methods of determining the occlusion plane are based a geometric relation to the anatomically fixed Camper plane, also called Ala-Tragus line, see for instance the above cited references Monteith (1985); Karkazis H C, Polyzois G L, Zissis A J (1986), Relationship between ala-tragus line and natural occlusal plane, Implications in denture prosthodontics, Quintessence Int 17:253-255; Karkazis H C, Polyzois G L (1987), A study of the occlusal plane orientation in complete denture construction, J Oral Rehabil 14:399-404; Kazanoglu A, Unger J W (1992), Determining the occlusal plane with the Camper's plane indicator, J Prosthet Dent 67:499-501; Santana-Penin U A, Mora M J (1998), The occlusal plane indicator: a new device for determining the inclination of the occlusal plane. J Prosthet Dent 80:374-375. Camper's plane is defined by three anatomically fixed points in the human skull, namely the spina nasalis anterior and the upper edge of the bony auditory channel (tragion) on the left and right cranial side. Camper's plane is virtually oriented parallel to the occlusion line, but may be corrected with a defined angle. The Camper plane is useful when producing dental prosthesis, for instance according to Maschinski G. Hasenan T, Illig U (2000), Lexikon Zahnmedizin Zahntechnik, München, Urban & Fischer, pp. 123, 560, 581; or Preti G, Koller M M, Bassi F (1992), A new method for positioning the maxillary anterior arch, orienting the occlusal plane, and determining the vertical dimension of occlusion, Quintessence Int 23:411-414.

Using the method of anatomically fixed reference points, it is not necessary to prepare a bite index of the patient for providing a planning with high accuracy.

The anatomically fixed reference points may also be anatomically fixed landmarks.

120 Dental Planning Based on Determined Anatomically Fixed Reference Points

Figure 10:
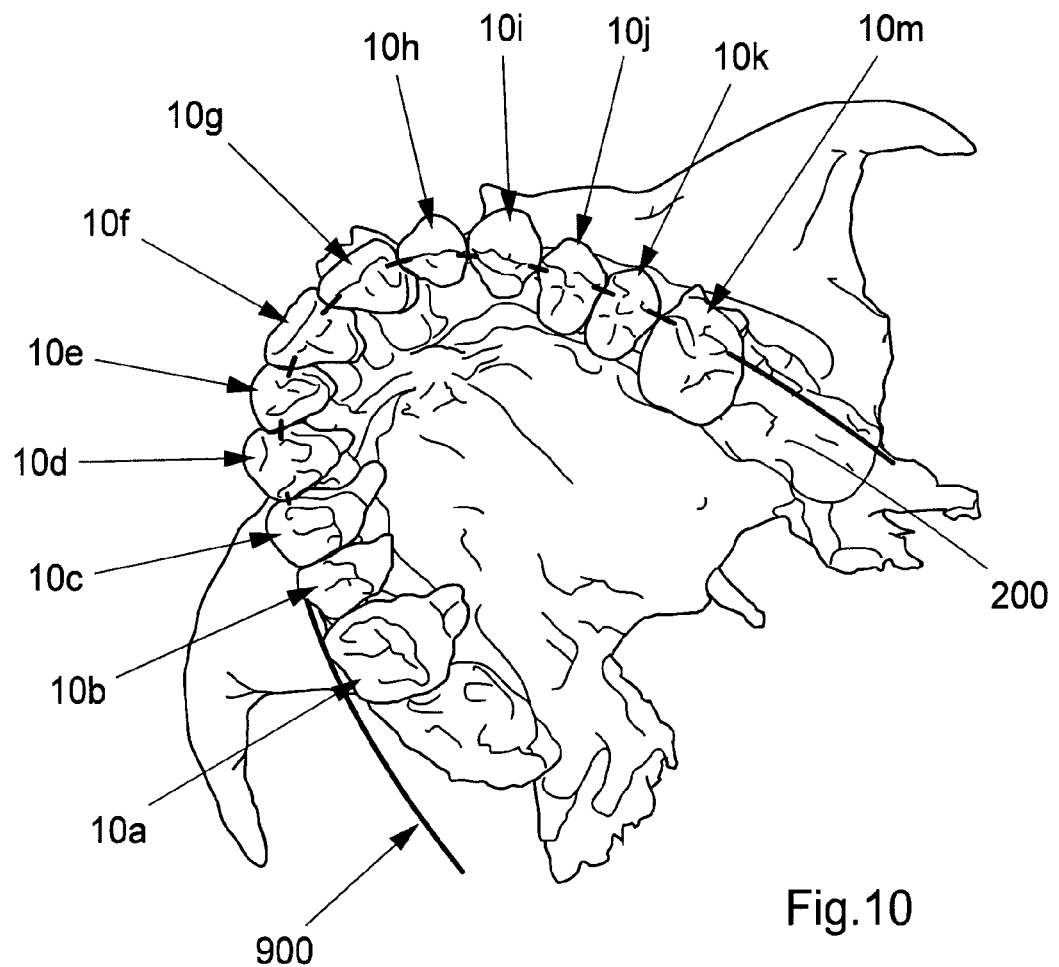
FIG. 10 is a schematic illustration in a view from below of the maxilla bone showing the calculated occlusion line and automatically aligned standard teeth between the occlusion line and the maxilla bone.

FIG. 10 is a schematic illustration in a view from below of the maxilla bone 200 showing the calculated occlusion line 900 and automatically aligned template teeth 10a-10m between the occlusion line 900 and the maxilla bone 200.

The template teeth are automatically or manually chosen from a library of virtual template teeth, dependent on the current dimensions of maxillary 200, the position of the teeth determined by the above describe mathematical calculations, the distance to occlusion line 900, bone density, each at the respective tooth position, etc. Also, adjacent teeth and the available total dental arch are considered when choosing suitable template teeth from the teeth library.

The virtual template teeth may be positioned and directed according to the principles described with reference to method step 110, e.g., in accordance with the method according to Staub.

For instance, the masticating surface, e.g., boundary surface at the occlusion line for every single tooth, may be calculated. Thereby a spatial position for each tooth is defined with reference to the occlusion line. A line of boundary masticating surfaces along the occlusion line may thus be calculated. Hence, a teeth set-up may be calculated according to the anatomically fixed reference points.

In this way, the position of one virtual template tooth or several virtual template teeth may be determined and an automatic alignment of Standard teeth between the occlusion line and the maxilla bone may be made.

In addition, the position of one or more of the virtual template teeth may be manually adapted, e.g., prior to a continued automatic planning of a positioning of further components for the dental restorative procedure under planning, such as dental implants, bridge frameworks, surgical templates, etc.

In case of planning a ceramic replacement tooth, one boundary surface, that has a spatial position, is at the occlusion line. A replacement tooth may comprise an outer dental veneering that is to be attached to a bridge framework for forming a bridge structure. The dental veneering has an inner boundary surface, that has a spatial position, serving as a connection interface towards a mating boundary surface, that has a spatial position, of a bridge framework (see FIG. 14c). The inner boundary surface has a defined spatial position, e.g., relative a bridge framework. The inner boundary surface of the dental veneering may be provided from the CAD data thereof. Hence, the boundary surface of the bridge framework, that has a spatial position, may be determined as the mating connection interface to the inner boundary surface of the dental veneering, which has a spatial position. The two boundary surfaces are adjoining at the connection interface.

130 Calculate Implant's Position and Directions

Figure 11:
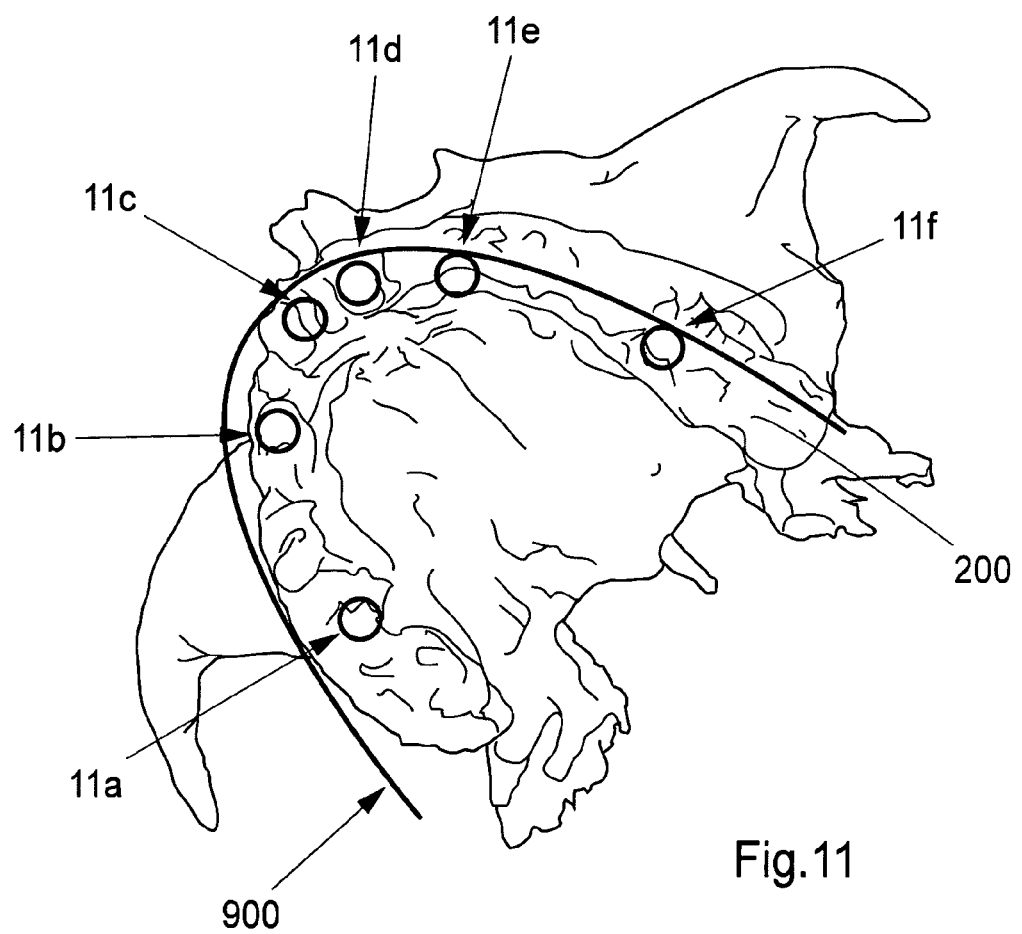
FIG. 11 is a schematic illustration in a view from below of the maxilla bone showing the calculated occlusion line and implants 11a-11f in the maxilla bone.

FIG. 11 is a schematic illustration in a view from below of the maxilla bone 200 showing the calculated occlusion line 900 and a plurality of implants 11a-11f in the maxilla bone 200.

A suggestion of the position of one or more dental implants, such as the plurality of dental implants 11a-11f in the illustrated example, may automatically be determined. This suggestion may be based on the data provided by the planned positions of the virtual teeth, as discussed above.

Embodiments of the automatic determination of implant positions will now be described in more detail.

By means of the planned position of virtual teeth the following method may be applied to determine the position of a dental implant in bone tissue of the patient.

The planned position of a virtual tooth provides a defined, determined position thereof in the craniooral space. The planned position of the virtually planned tooth is based on the occlusion line, e.g., the top end of the virtual tooth is thereby defined. Furthermore, the tooth has a determined position along the dental arch, as well as a defined orientation in the craniooral space.

Jaw bone tissue at locations of extracted or lost teeth, e.g., of edentulous patients, changes over time in comparison with natural jaw bone tissue of patients with natural teeth. The jaw bone tissue shrinks, but may be regenerated by osseoinductive methods. When positioning a dental implant in the area of the virtual root channel of the virtually planned tooth, the dental implant may be positioned too far away from existing jaw bone tissue.

Therefore, a defined space may be defined by the virtually planned tooth within which the dental implant may be implanted in available bone tissue. The defined space may be of cylindrical form and defines the boundaries in vertical direction along which the implant may be positioned. In longitudinal direction the position of the implant may be varied, e.g., depending on remaining anatomical bone tissue, as provided from the patient data. Thus, a space defining a degree of freedom for positioning the dental implant is defined.

The dental implant may be positioned within this space according to a method based on centering the center of gravity of the dental implant in the remaining bone tissue at a defined distance from the boundaries thereof. Thus, sufficient bone tissue is provided for ensuring a secure fixation of the dental implant in the remaining bone tissue. Alternatively, if it is detected that sufficient bone tissue is not available, alternative implant sizes may be chosen.

Centering the center of gravity of the dental implant in the remaining bone tissue may be done as follows. By surface matching, the form of the jaw bone tissue is detected. A top point of the jaw bone tissue is detected, e.g., by a surface finding algorithm. Further points on the surface of the bone tissue are detected laterally at a certain vertical distance from the top point.

The position of the dental implant is then determined in relation to these three defined points. For instance the center of gravity is positioned on a line between the two lateral points and longitudinally below the top point. A defined distance from the surface of the jaw bone tissue is thus ensured and the dental implant is reliably anchored in the jaw bone tissue.

Another way may be to project a plurality of vectors along a defined trace from the center of gravity of the dental implant towards the surface of the bone tissue. This is done for ensuring that the bone surface is found in relation to the position of the implant or to ensure that the implant is positioned correctly or sufficiently far from the boundaries of the bone tissue.

The length of the vectors may be chosen as the distance of the center of gravity of the implant to the top of the implant. The top of the implant is advantageously positioned at the top point or ridge of the jaw bone tissue.

The defined trace along which the plurality of vectors is traced may have different forms from the initial point of the center of gravity, e.g., cylindrical, conical, in one or more planes. This may be done in order to ensure e.g., a defined distance from anatomical structures and/or other dental restorations or implant components.

The vectors may be adaptively defined. For example, a first vector is sent out in 45 degrees direction, and a second vector is sent out in 135 degrees direction. Then it is ensured that these vector meet bone surface and have substantially same length.

The surface of the virtual jaw bone tissue may be defined by a plurality of polygons. The virtual jaw bone tissue may be modeled as a 3D object from these polygons.

In case a vector of the trace meets or cuts through such a polygon, this information may be used for virtually re-orienting the implant in the bone tissue during planning. The implant may thus for instance be centered in the available anatomical jaw bone tissue.

Thus it may be ensured that the implant is positioned with sufficient bone tissue surrounding the latter.

Hence, the automatic positioning of the implant may be object or surface based.

Based on the data of the first boundary surface of the veneering, that has a spatial position at the occlusion line, and the spatial position of the teeth, or boundary surfaces thereof, calculated from the identified anatomically fixed reference points, sufficient data is provided for suggesting a position of the implant. Other parameters that may be taken into consideration are e.g., bone density of jaw bone tissue at the implantation site, extension of nerves and blood vessels, etc.

Figure 12A:
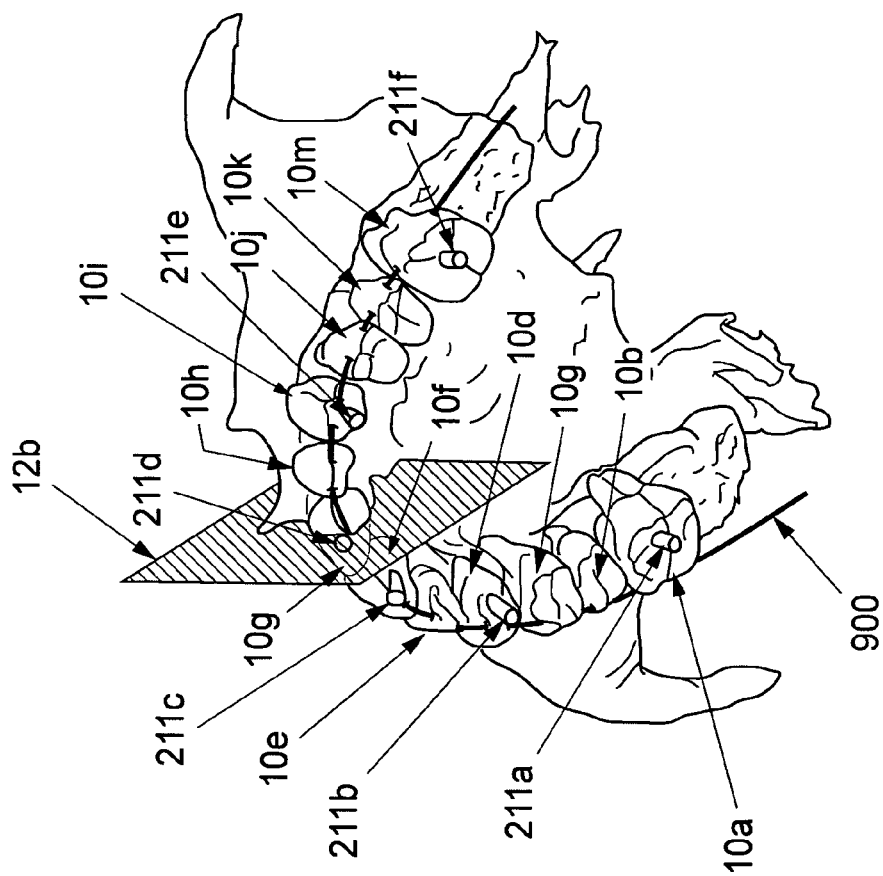
FIG. 12a is a schematic illustration in a view from below of the edentulous maxilla bone showing the calculated occlusion line, the position and direction of implants, and automatically aligned standard teeth.

FIG. 12a is a schematic illustration in a view from below of the edentulous maxilla bone 200 showing the calculated occlusion line 900, the position and direction of implants 11a-11f, and automatically aligned standard teeth 10a-10m. The implants 11a-11f are illustrated by virtual markers 211a-211f going through the central longitudinal axis of each implant. The implants themselves are hidden under the illustrated standard teeth at the corresponding implant position, respectively. The virtual markers 211a-211f illustrate the direction into which a surgical template will be provided with drill guiding bores for precision drilling of bores in the jaw bone tissue where the implants are to be installed during a surgical procedure subsequent to the virtual planning and production of dental components for the surgical procedure.

Figure 12B:
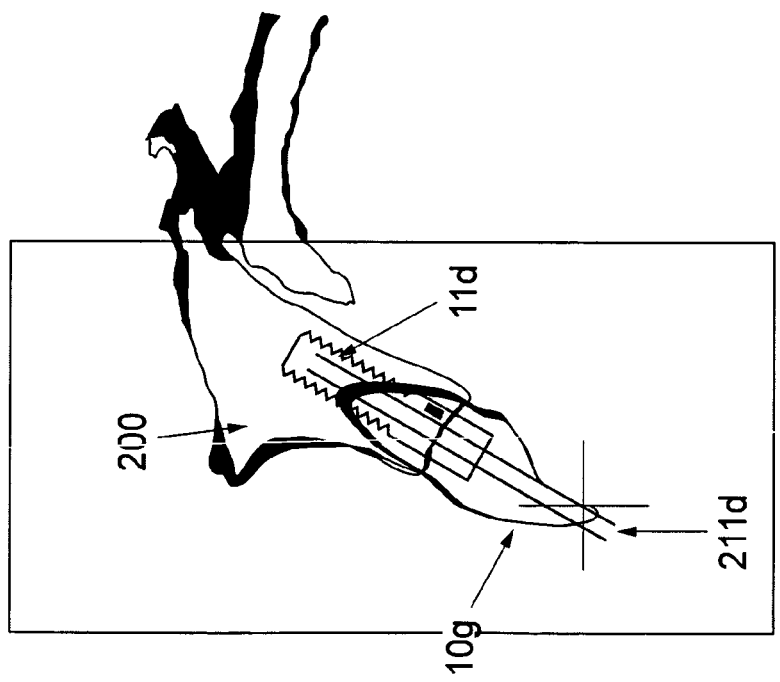
FIG. 12b is a cross sectional view through the plane shown in FIG. 12a, at tooth pos. 21 with an overlayed implant.

FIG. 12b is a cross sectional view through the plane 12b shown in FIG. 12a, at tooth pos. 2-1 (EU) with an overlayed implant 11d in the maxillary bone tissue 200.

For instance, the surface of the maxillary bone tissue is determined and the positioning of a coronal end of an implant is positioned at the ridge of the maxillary bone. Furthermore, available bone tissue volume, bone tissue quality, existing implants, etc. may be considered. The implant is positioned in the bone tissue in dependency of the planned positions of the teeth, as discussed above.

The presurgical planning may be made computer based. The planning may be made automatically or in an interactive way with a user. Planning of the dental restoration may in the latter case be made visually on a display of a medical workstation, e.g., of the system described below with reference to FIG. 31, in an interactive way manipulated by user input. For instance the position and direction of dental implants in jaw bone is virtually presented on the display visualizing the jaw bone structure where a dental restoration is to be made. During planning care has to be taken that for instance no nerves are damaged or that the dental implant is positioned in as much dense bone as possible, in order to ensure a successful surgical installation of the dental implant. Hence, the user may virtually manipulate or accept placement of dental implants in advance of final placement. The implant's position, angulation, type of implant, length, in relation to final teeth restoration, may in an interactive manner be manually fine tuned.

When the implant is positioned, a fixed outer boundary surface of the implant, or a boundary surface of an abutment that is attached to the implant, is determined. Now the intermediate structure between the implant and the veneering will be provided in order to finalize planning of the dental restoration.

140 Automatic Generation of Implant Bridge Framework

At this stage, the spatial position of the dental restoration is defined (step 120) and the spatial position of the implant is defined (step 130). Boundary surfaces of the veneering and the implant, and the spatial positions thereof, are determined and known. The structure in between the veneering and the implant is now virtually planned. This is made in relation to the spatial positions of the implant and the remaining dental restoration, e.g., an interface between the implant and the veneering is calculated and the virtually assembled structure may then be manually fine tuned.

For this purpose, boundary surfaces, having a spatial position, of the veneering and the implant are used.

Figure 13A:
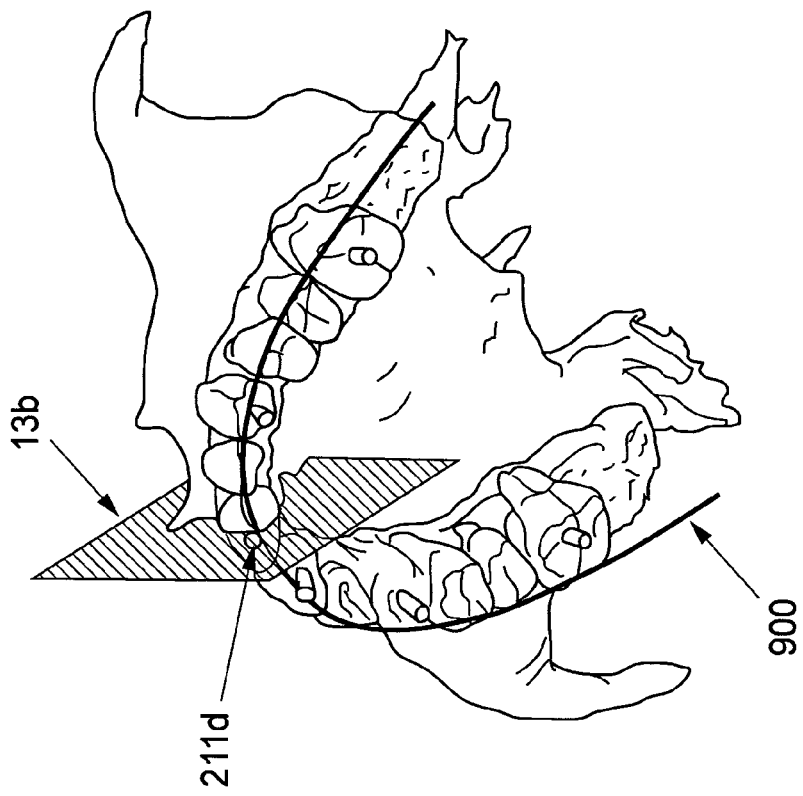
FIG. 13a is a schematic illustration in a view from below of the maxilla bone showing the calculated occlusion line, the position and direction of implants, and a twelve unit implant bridge framework on the six implants.

FIG. 13a is a schematic illustration in a view from below of the maxilla bone 200 showing the calculated occlusion line 900 and a twelve unit implant bridge framework 20 on the six implants 11a-11f.

Figure 13B:
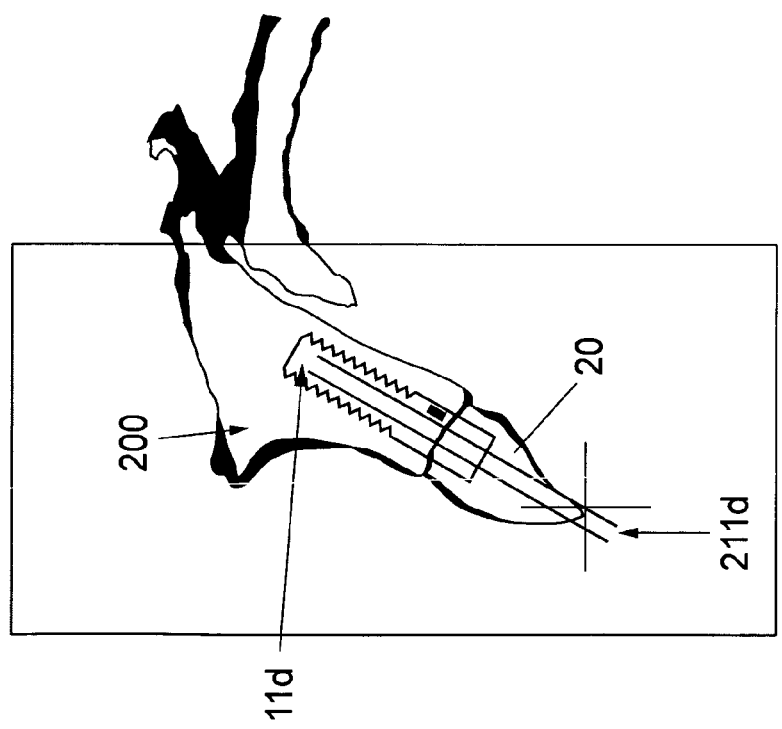
FIG. 13b is a cross sectional view through the plane 13b shown in FIG. 13a, at tooth pos. 21 with an overlayed implant.
Figure 14C:
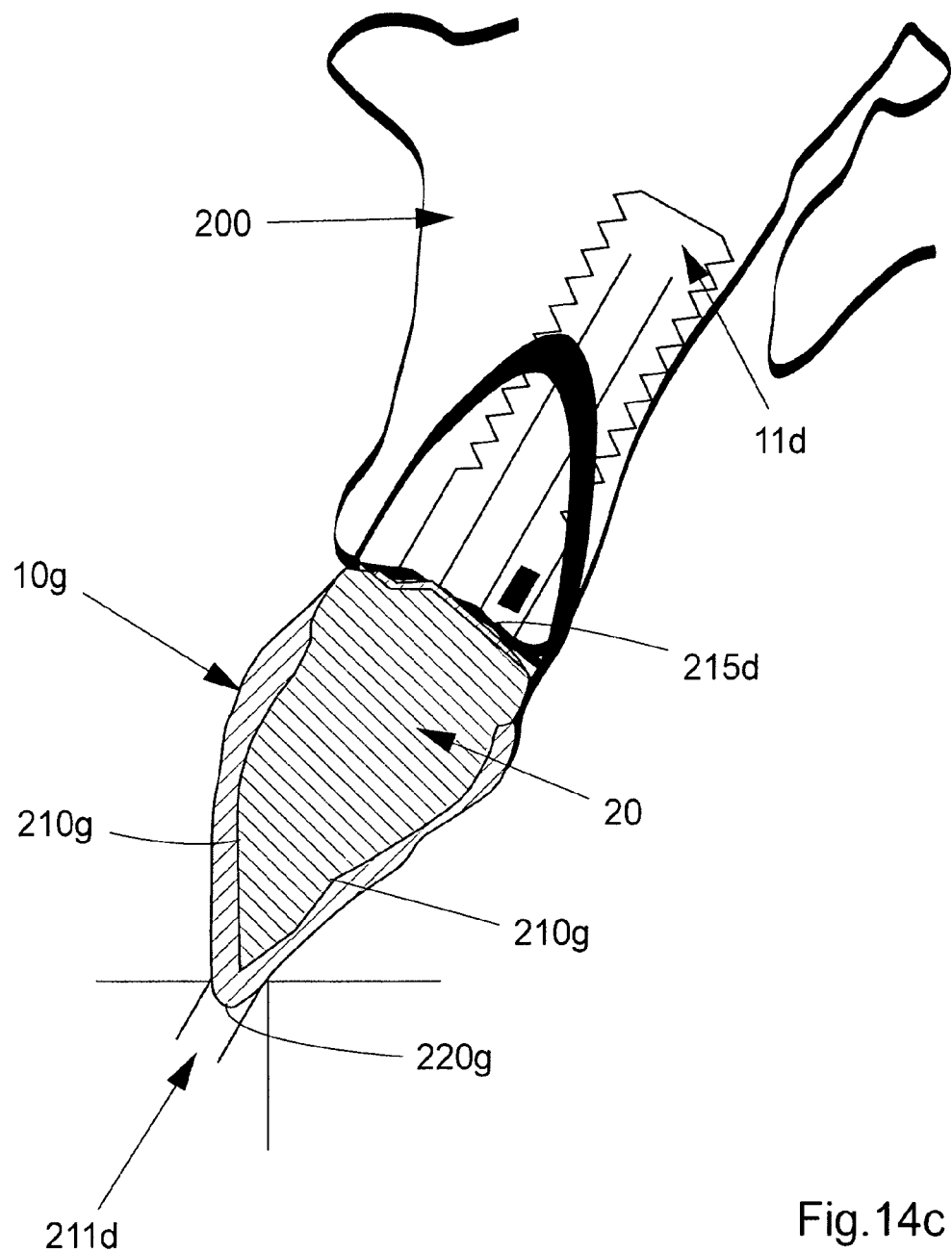
FIG. 14c is a cross sectional enlarged view corresponding to FIG. 14b.

FIG. 13b is a cross sectional view through the plane 13b shown in FIG. 13a, at tooth pos. 2-1 (EU) with an overlayed implant 11d.

FIG. 14a is a schematic illustration in a view from below of the maxilla bone 200 showing the calculated occlusion line 900, the position and direction of implants 11a-11f, and a twelve unit implant bridge framework 20 on the six implants 11a-11f, as well as the automatically aligned standard teeth 10a-10m.

FIG. 14b is a cross sectional view through the plane 14b shown in FIG. 14a, at tooth pos. 21 with an overlayed implant 11d, and the bridge framework 20, wherein the boundary surfaces interfacing therebetween, and which have spatial positions, are shown.

As mentioned above, the veneering has an outer boundary surface, which has a spatial position, at the occlusion line 900, and an inner boundary surface, that has a spatial position, serving as a connection interface 210g between the veneering 10g and an outer boundary surface, that has a spatial position, of a bridge framework 20. At the same time, the bridge framework 20 has a further boundary surface, that has a spatial position, oriented towards the implant 11d, serving as a connection interface with the latter. The implant 11d has a top boundary surface, that has a spatial position, serving as the connection interface 215d with further boundary surface of the bridge framework 20. The boundary surfaces and connection interfaces are illustrated in the enlarged illustration shown in FIG. 14c.

When fine tuning the position of the implant or the veneering at this stage, an automatic adaptation of the remaining parts of the dental restoration are made. For instance, when manually fine tuning the position of a dental implant, the connection interface 215d is automatically adapted by recalculating the corresponding boundary surface of the bridge framework 20. Furthermore, the boundary surface on the opposed side of the bridge framework 20, at the connection interface 210g to the veneering's inner boundary surface, is automatically adapted to the manually induced fine tuning of the position of the implant. Thus, the bridge structure is automatically adapted. Manual fine tuning of other parts of the dental restoration lead to corresponding automatic changes of the boundary surfaces of the remaining units thereof.

FIGS. 18 to 22 further illustrate the virtual planning for the case of an edentulous patient.

Figure 18:
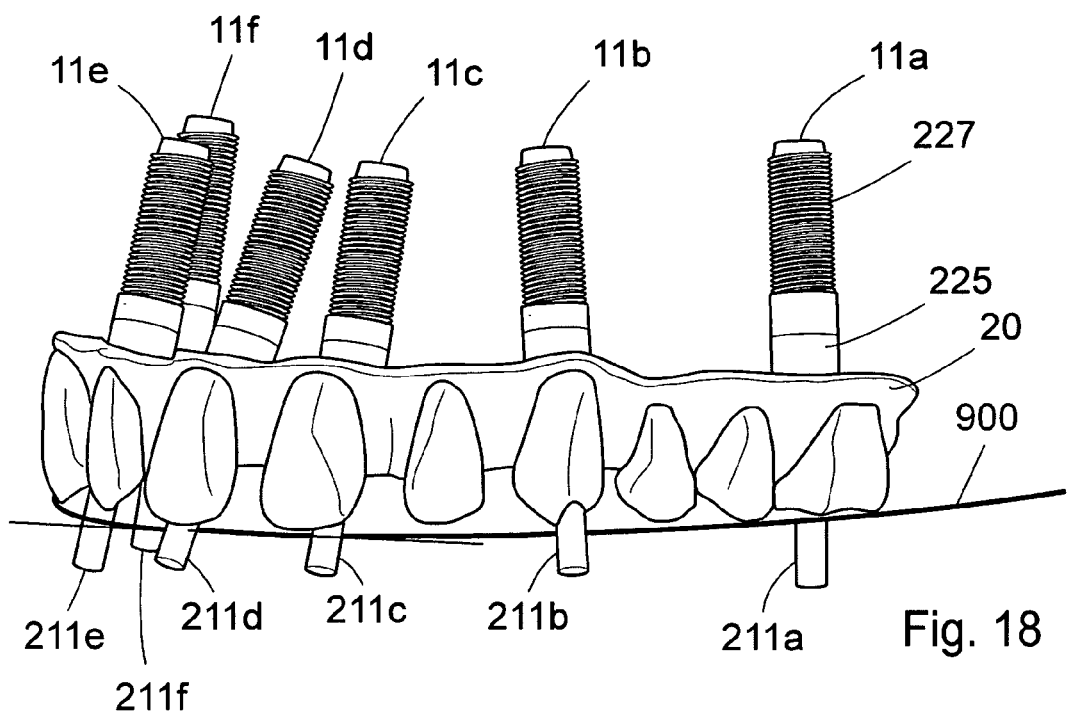
FIG. 18 is a schematic illustration of a bridge framework, implants and an occlusion line in a perspective view.

FIG. 18 is a schematic illustration of the virtually planned bridge framework 20, implants 11a-11f and occlusion line 900 in a perspective view. Collars 225 of the bridge framework 20 are illustrated in FIG. 18. The collars 225 are arranged to abut against the top surface of the dental implants, respectively. Each of the top surface of the collars 225 and the top surface of the dental implants has a spatial position. When assembled, the two spatial positions are adjoining at the connection interface between the two dental units. Furthermore the collars 225 provide an adjustment to soft tissue thickness. Implants 11a-11e are provided with threads for threadibly mounting into pre-prepared bores in the jaw bone tissue. The virtual markers 211a-211f are shown more detailed in FIG. 18 and FIG. 19, indicating the central longitudinal axis of each implant, respectively. FIG. 20 is a schematic illustration of a detail of the bridge framework 20, implants 11a, 11b and the occlusion line 900 of FIG. 18 in an enlarged perspective view.

Figure 19:
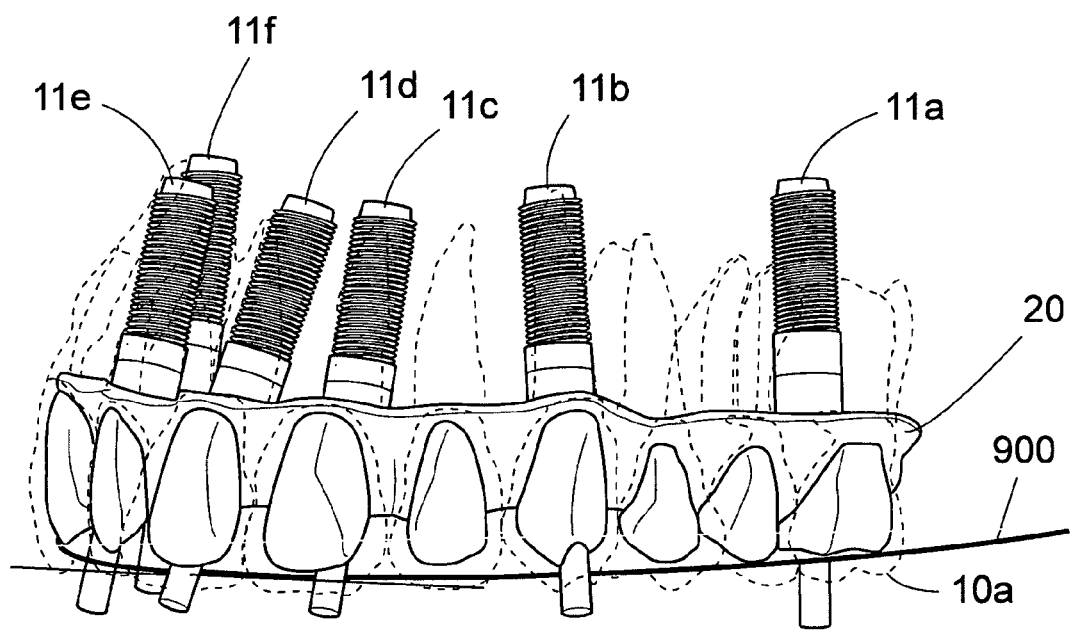
FIG. 19 is a schematic illustration of a bridge framework, implants, library virtual teeth, and an occlusion line in a perspective view.
Figure 20:
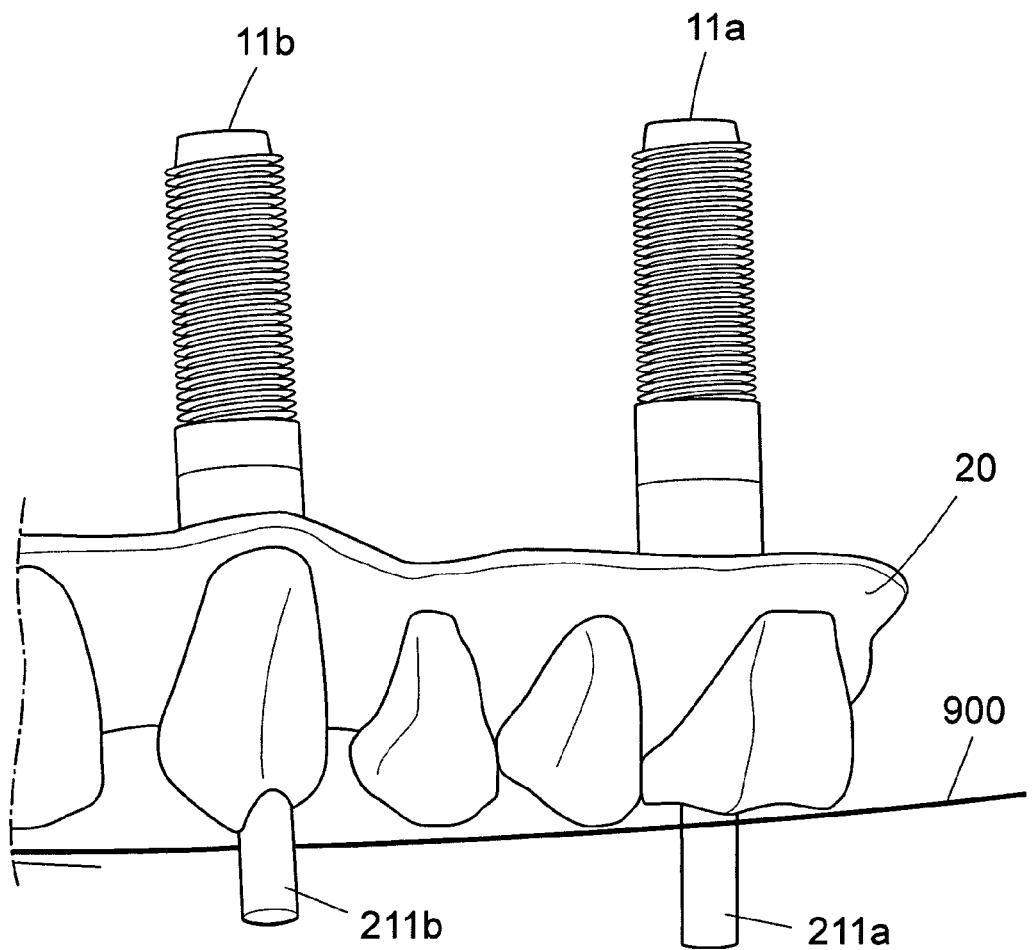
FIG. 20 is a schematic illustration of a detail of the bridge framework, implants and an occlusion line of FIG. 18 in an enlarged perspective view.

In FIG. 19 template teeth are added to the illustration, wherein only tooth 10a is provided with a reference sign for the sake of lucidity. The template teeth are shown with dashed lines.

Figure 21:
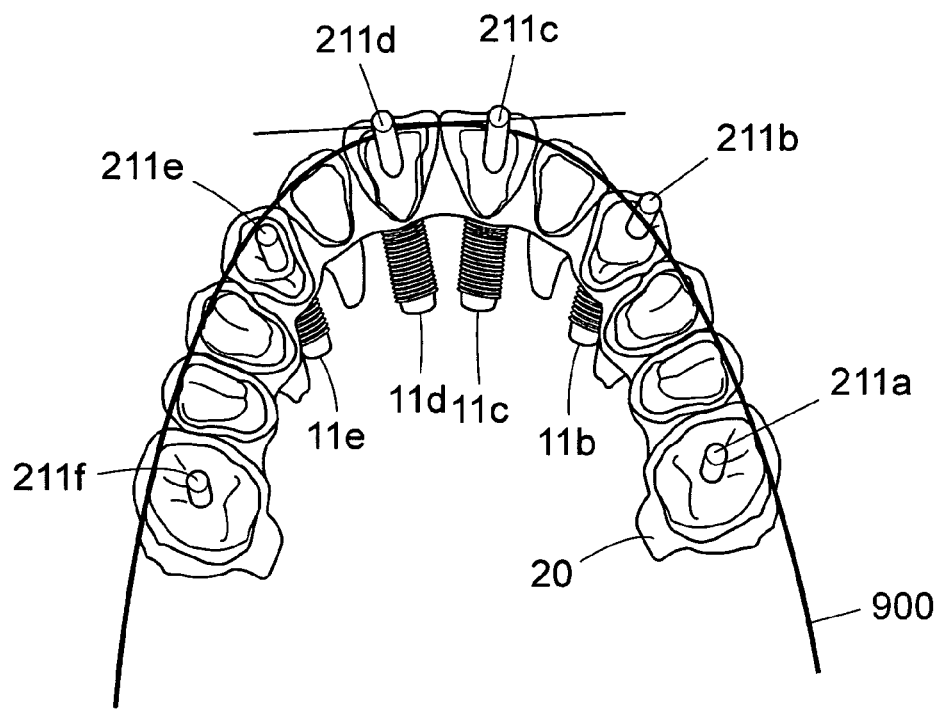
FIG. 21 is a schematic illustration of a detail of the bridge framework, implants and an occlusion line of FIG. 18 in a perspective view from below.
Figure 22:
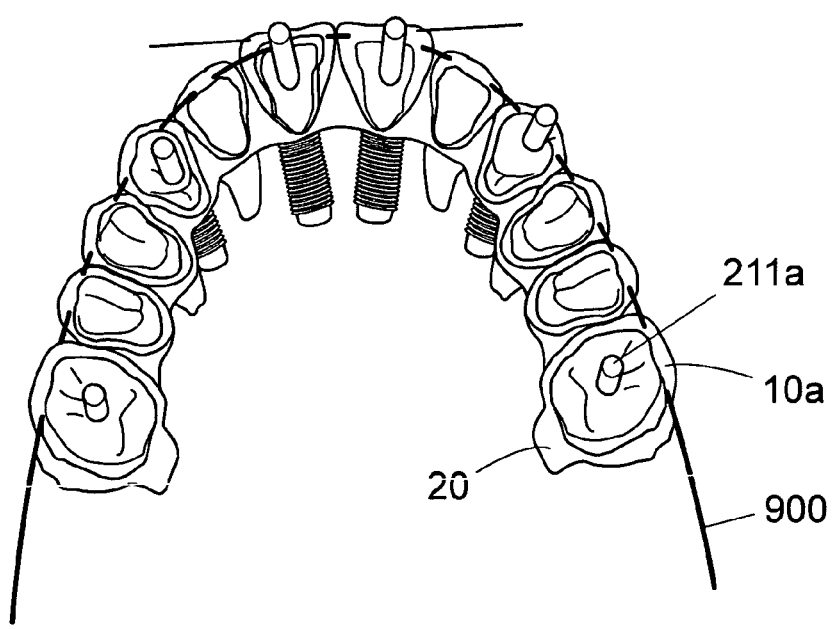
FIG. 22 is a schematic illustration of the bridge framework, implants, library virtual teeth, and an occlusion line of FIG. 20 in a perspective view from below.

FIG. 21 is a schematic illustration of a detail of the bridge framework, implants and occlusion line of FIG. 18 in a perspective view from below. In FIG. 22 template teeth from the library of virtual teeth are added to the illustration, wherein it is shown how the teeth are positioned in relation to the occlusion line 900.

150 Approximation of the Final Restoration

FIG. 14b shows bridge structure comprising a bridge framework 20 and veneering at tooth position 2-1 (EU).

Figure 23:
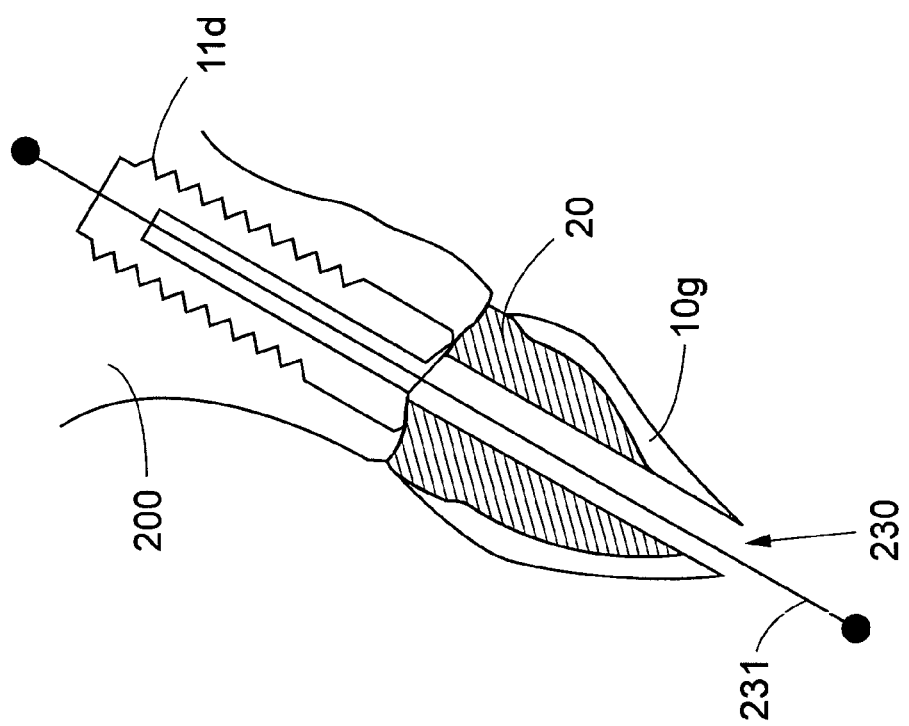
FIG. 23 is a cross sectional view through a virtually planned dental restoration and dental implant in jaw bone tissue illustrating an exit hole.

FIG. 23 is a cross sectional view through a virtually planned dental restoration comprising the dental implant 11d in the jaw bone tissue 200, illustrating an exit hole 230 through the bridge framework 20 and template tooth 10g. The direction of the exit hole, which during subsequent installation of the dental restoration is used for access of a retaining screw attaching the bridge framework to the implants, is indicated by a virtual marker 231. The virtual marker 231 extends along the longitudinal axis of the dental implant 11d and the position of the virtual marker 231 may be modified by user input, e.g., by dragging the illustrated dot at an end of the marker 231 by mouse interaction. In the illustrated case the exit hole shown in FIG. 23 is automatically planned and situated visibly in the buccal side of the tooth 10g. The user may desire to hide this exit hole due to esthetical reasons. For this purpose, a user manipulation may result in a modified virtual model of the dental restoration as illustrated in FIG. 24.

Figure 24:
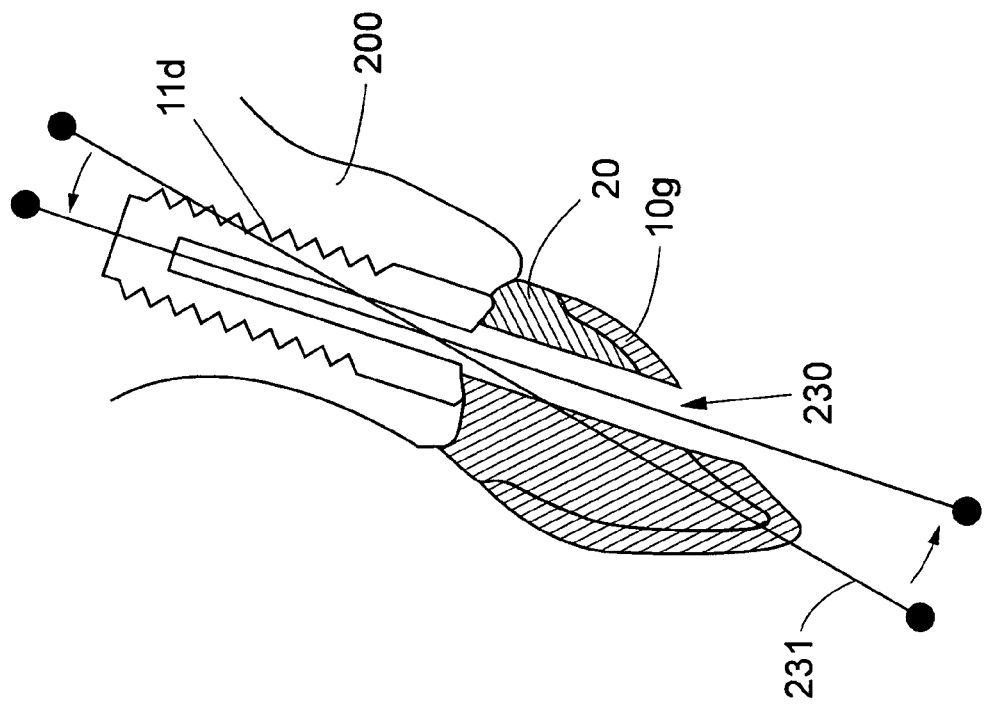
FIG. 24 is a cross sectional view through the dental restoration and dental implant of FIG. 23, wherein the position of the dental implant is modified such that the exit hole is moved to the back of the dental restoration.

FIG. 24 is a cross sectional view through the dental restoration comprising the dental implant 11d of FIG. 23, wherein the position of the dental implant 11d is modified such that the exit hole 230 is moved to the lingual side of the tooth 10g. The spatial location of the bridge framework 20 and the top position of the tooth 10g at the occlusion line are unchanged. However, the implant 11d is now angled in the bone tissue 200 such that the exit hole 230 along the longitudinal axis of the dental implant 11d is moved to a hidden location, e.g., the hole is not visible when the final product is implanted in the patient and the patient smiles. The top surface of the implant 11d is unchanged, but the change made to the spatial position thereof in bone tissue 200 has resulted in an automatic adaptation of the bridge framework design and also of the corresponding veneering to the new situation. More precisely, the top position of the tooth 10g at the occlusion line defines a first boundary surface, which first spatial position is determined. The top surface of the implant 11d is a second boundary surface, which second spatial position is determined. The design of the dental veneering and of the bridge framework between these two locked boundary surfaces is automatically adapted to fit between the two boundary surfaces, while maintaining other requirements, such as distance to adjacent teeth etc. The spatial position of the boundary surface between the bride 20 and the dental veneering is determined relative the first and second spatial positions.

Once the user confirms these changes, production of the dental restoration and a drill guide will be based on this new data.

The dental veneering may automatically be produced from the available data.

Furthermore, coloring of the veneering may be made automatically. Various ceramic powders may be virtually planned on the screen. Such techniques are detailed described in the international patent application PCT/SE2005/001406 of the same applicant as the present application, filed on Sep. 23, 2005, which hereby is incorporated herein by reference in its entirety.

Hence, the system may be used for a fully automatic generation of dental restorations. Manual adaptation to specific patient situations, choice selectable from dental restoration component libraries, or other user desires may be performed.

160 Surgical Template Production

Figure 15:
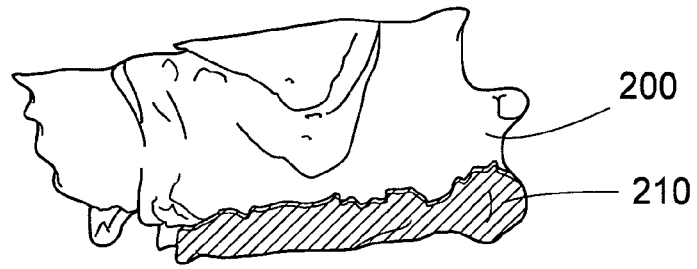
FIG. 15 is a schematic illustration of the maxilla bone and soft tissue in a lateral view.
Figure 16:
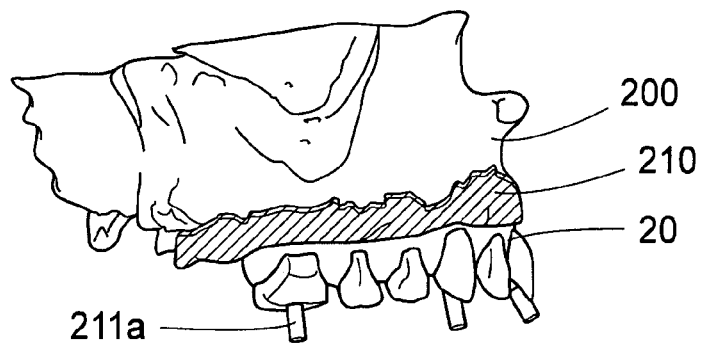
FIG. 16 is a schematic illustration of the maxilla bone and soft tissue and the implant bridge framework in a lateral view.

FIG. 15 is a schematic illustration of the maxilla bone 200 and soft tissue 210 in a lateral view. As described above, with reference to step 100, methods of acquiring patient data including bone tissue and soft tissue comprise MR scanning the craniofacial portion of the patient; using surface probes to determine a thickness of soft tissue in the oral cavity; soft tissue may be extracted from CT scan data by suitable thresholding algorithms; input data from several input sources may be matched; etc. An example of a rendered illustration of maxillary bone tissue 200 and soft tissue 210 is shown in FIG. 15. In the illustrated example, the maxilla of the patient is edentulous. The soft tissue 210, as shown in FIGS. 15 and 16, may be determined from a single CT scan. The soft tissue may in this case be extracted from such CT data, based on the difference of acquired soft tissue and acquired air.

FIG. 16 is a schematic illustration of the maxilla bone 200 and soft tissue 210 and the implant bridge framework 20 in a lateral view. Here, a final check of the implant bridge framework 20 design is virtually made. The user is presented with a visualization of a bridge framework 20 and positions of implants, marked by markers 211a-211f, together with soft tissue 210. The bridge framework 20 is abutting implants 11a-11f at respective boundary surfaces forming connection interfaces. The bridge framework 20 is also resting against the soft tissue and final corrections to the specific patient situation may be virtually made at this stage, before data is used for production of non-virtual dental components. When final manual corrections are made, a surgical template may be produced.

Figure 17:
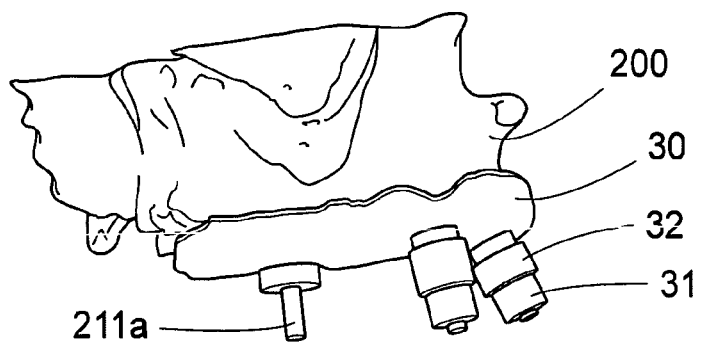
FIG. 17 is a schematic illustration of the maxilla bone and a surgical drill guide having drill guide bores.

FIG. 17 is a schematic illustration of the maxilla bone 200 and a surgical template 30 having drill guide bores 31. The surgical template 30 serves as a drill guide during a dental restorative procedure, during which a dental restoration is implanted in the oral cavity of a patient according to known methods. The surgical template is virtually planned from the final dental restoration data that is available at this stage. Guide sleeves 32 for guiding of drills are schematically illustrated. The guide sleeves 32 of the surgical template 30 are used for directing a drill through the soft tissue and into the jaw bone tissue of the patient. Guide sleeves 32 have a defined direction in line with the virtually planned position of an associated dental implant. Furthermore, the top surface of guide sleeves 32 are arranged as a collar having a stop shoulder for the drill and are arranged at a defined distance from the top surface of a dental implant to be implanted into the bore drilled by the drill. Thus, the depth of the bore is controlled by providing suitable drills that enter into the guide sleeve until abutting to the stop shoulder. The top surface of the stop shoulder is a boundary surface. Thus precise bores are provided for subsequent implantation of dental implants that will have a defined orientation and position in bone tissue.

When the pre-surgical planning is made, production of dental restorations and/or products related to said pre-surgical planning, such as surgical templates, may be made. For instance, the soft tissue surface and implant position are converted to production data for a drill guide to be used during a surgical implant procedure.

Based on the above described automatic or manually fine tuned virtual presurgical planning, a surgical template may be fabricated, e.g., using rapid prototyping techniques. The surgical template is used in a known way for creating suitable bores for mounting of dental implants, to which the dental restorations will be fixed, at the planned position and with the planned orientation.

Data for products produced by stereolithography, such as a surgical template, may be saved in a suitable format, such as STL. STL (Standard Tessellation Language) files may be imported and exported by a variety of software packages. The STL file is especially suitable for rapid prototyping. This format approximates the surfaces of a solid model with triangles for rapid prototyping. Other data formats than STL suitable for production of dental restorations and related products may alternatively be implemented. Rapid prototyping takes virtual designs from computer aided design (CAD), transforms them into cross sections, still virtual, and then creates each cross section in physical space, one after the next until the model is finished.

The surgical template thus produced provides a good patient fit with high accuracy.

170 Dental Restoration Production

In step 170 of the method, a dental restoration is produced based on the data provided.

A physical patient model may be manufactured from the data provided by the virtual planning, if so desired. A patient model may for instance be used for veneering, in case veneering is desired to be performed manually. Production of a patient model and an articulator are described in Swedish patent applications nos. SE 0602271-9 and SE 0602273-5, which are incorporated herein in their entirety by reference, filed by the same applicant as of the present application. However, this step may be omitted, as the available data provided by the above described automatic virtual planning provides sufficient precision for both presurgical planning and production of surgical templates and dental restorations.

In step 170 of the method, a dental restoration is produced directly from that data provided by the presurgical planning.

Veneering of the dental restoration may be performed in a conventional way. For this purpose a physical patient model may be used. In another embodiment design of the final restoration is made virtually based on the above method steps, whereby manual veneering is no longer necessary.

Finally, the dental restoration is installed in the patient. More precisely, the surgical template produced as described above, is used for providing one or more bores, each receiving a dental implant. Thanks to the high precision with which the surgical template is produced, dental implants are fitted very precise into the jaw bone tissue. Thus a thorough basis is provided for the dental restoration that is then attached to the dental implant in a known manner.

By using the above described method, no casting, sectionizing, and pinning of a plaster model is needed. This provides for faster turnaround times when planning and carrying out dental restorative procedures.

Hence, a very precise positioned dental restoration is provided in a very economical and time saving manner.

Bridge frameworks may be fully automatically planned and produced.

In some treatments even the surgical template is no longer necessary. For instance when producing a coping, such as for a crown, a bridge framework, or a bridge structure, to be attached to a dental preparation, the coping may be produced directly based on the boundary surface and connection interface calculations during the automatic virtual presurgical planning.

In other embodiments a dental restoration for a partly toothless patient and a dental restorative procedure, as well as corresponding products, are virtually planned, which is now described in detail with reference to FIGS. 25 to 30.

Figure 25:
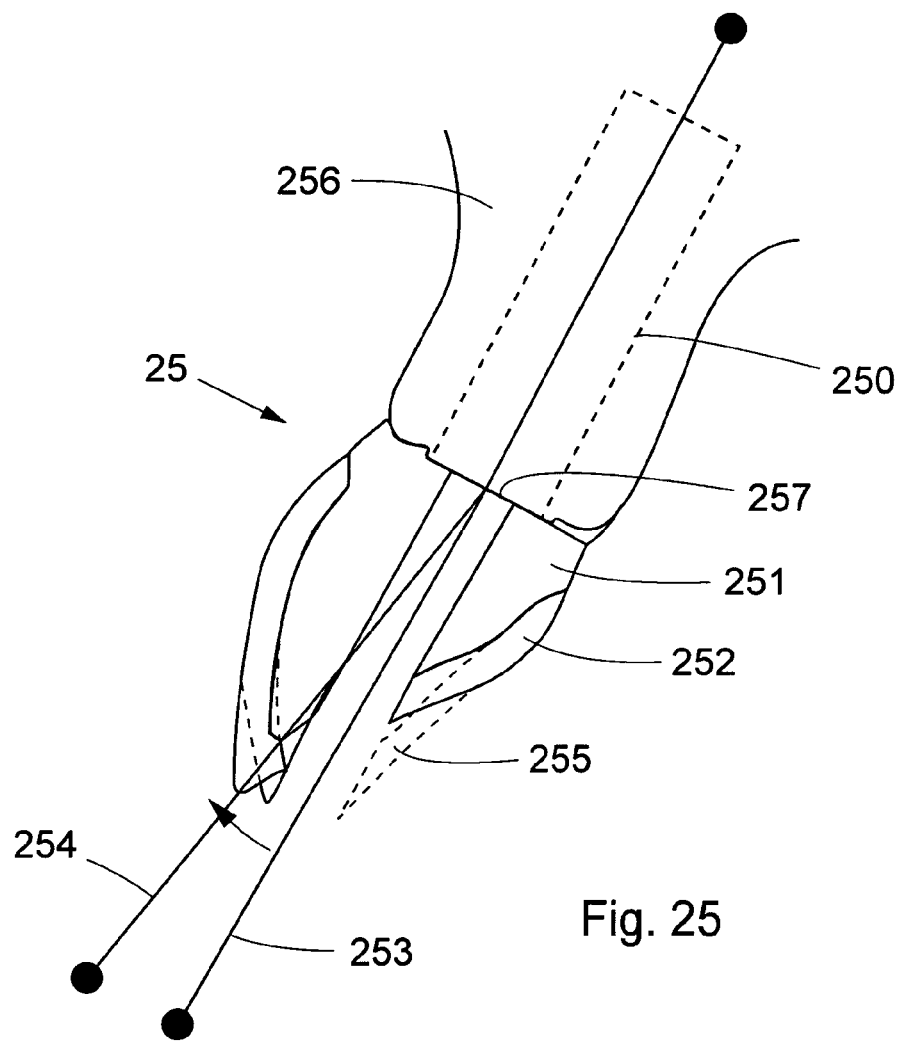
FIG. 25 is a cross sectional view through a dental restoration and a dental implant, wherein the position of the dental implant is fixed and the dental restoration is virtually modified with automatic adaptation of a bridge structure comprising a bridge framework and a veneering.

FIG. 25 is a cross sectional view through a dental restoration 25 comprising a dental implant 250 that is previously implanted in a jaw bone tissue 256 of a patient. The dental implant 250 is healed into the jaw bone tissue 256. Data for the position of the dental implant may for instance be provided by suitable medical imaging methods, and/or a dental impression of the oral cavity registering the coronal end 257 of the dental implant 250, and/or of data that perhaps is available from a previous dental planning for the dental implant 250. Thus, the position of the dental implant 250 is fixed and the position of the coronal surface 257 is locked for virtual planning of the dental restoration 25. In this case an automatic planning of a bridge framework 251 and a veneering 252 resulted in a suggested position thereof as shown by the dotted line 255. A bore is present along the longitudinal axis 253 of the dental implant 250. In FIG. 25 it is illustrated how the orientation of the tooth to be restored and affixed to the dental implant 250 is virtually dynamically modified, based on input from a user, to an alternative position, e.g., by interactively drawing a planning line 254, e.g., by means of a mouse, in the direction of the arrow shown in FIG. 25. The modification may be desired by a user du to the local dental situation of the patient. The result of the recalculated dental restoration 25, after the user manipulation input, is illustrated by the continuous line of the bridge framework 251 and the veneering 252. The position of the bore therein towards the dental implant is unchanged, as the position of the coronal surface 257 is locked, and in order to facilitate attachment of the bridge framework or bridge structure to the dental implant 250. The dental restoration 25 is thus virtually modified with automatic adaptation of the bridge structure comprising the bridge framework 251 and the veneering 252.

A procedure for finding a final connection interface may be controlled by virtually morphing the spatial positions of the two boundary surfaces of elements of a dental restoration. With reference to FIGS. 26A to 26C, the use of controlled morphing is now explained in more detail. Morphing is an interpolation technique used to create from a source object to a target object a series of intermediate objects that change continuously to make a smooth transition from the source to the target object. Morphing is for instance done in three dimensions by varying the values of three-dimensional pixels, or by transforming the geometry of three dimensional models and creating intermediate objects which are all clearly defined three-dimensional objects. In this context a connection interface between two units of a dental restoration may be virtually optimized by morphing. In FIG. 26A a dental restoration 26a is illustrated. The dental restoration 26a has a known structure comprising a coping 261 and a crown 262, which are attached to a dental restoration element 260. The dental restoration element 260 may be a dental preparation of an existing tooth, see FIG. 29, or a cap of a dental implant, see FIG. 30C. As is illustrated in FIG. 26A, the coping 261 has an inner surface at a first connection interface 261a with the dental restoration element 260, and an outer surface at a second connection interface 261b with the crown 262. The outer surface of coping 261 is positioned at an offset from the first connection interface 261a, e.g., the second connection interface 261b extends in parallel to the outer surface of the dental restoration element 260 at the connection interface 261a. Given the geometry of the second connection interface 261b, the inner surface of the crown 262 has apically a defined geometry at the second connection interface 261b. The outer surface of the crown 262 is underlying geometrical restrictions defined coronally by the occlusion and laterally by adjacent teeth. By providing the coping in the described offset form, the porcelain of the crown 262 may not be supported optimally by the coping 261, leading to irregularly distributed chewing stress of the crown 262.

This situation may be improved by morphing the second connection interface 261b towards the outer surface of the crown 262, which is illustrated in FIG. 26B. The dental restoration 26b has an improved second connection interface 263b. By using a morphing technique, the source objects being the second connection interface 261b and the target object being the outer surface of the crown 262, a series of intermediate objects is calculated to form a smooth transition therebetween. The improved second connection interface 263b is chosen as one of the intermediate objects of the morphing process, providing a better support for the crown 264. The crown 264 has an inner surface matching the improved second connection interface 263b. The outer surface of crown 264 is still defined by the same requirements of the surrounding structures in the oral cavity or by modifying a suggested restoration.

In FIG. 26C the outer shape of a dental restoration element 265 is defined by such a morphing technique, whereby a separate coping is omitted. In more detail, the coronal outer surface of dental restoration element 260 is morphed to the outer surface of the crown 262 and an intermediate object shape is chosen to provide a more advantageous support of the crown 266. A single connection interface 265b is thus defined, and improved dental restoration element 265 and crown 266 are provided.

In any case it should be observed that a minimal material strength is preserved when determining the connection interfaces. The above mentioned template teeth in the virtual teeth library may be adapted to tolerate such manipulations, e.g., by having a predefined minimal material thickness at an arbitrary point of a template tooth.

In other embodiments other dental restoration elements may be optimized or defined by morphing techniques, e.g., bridge frameworks. A similar technique to morphing is known as warping.

Figure 27A:
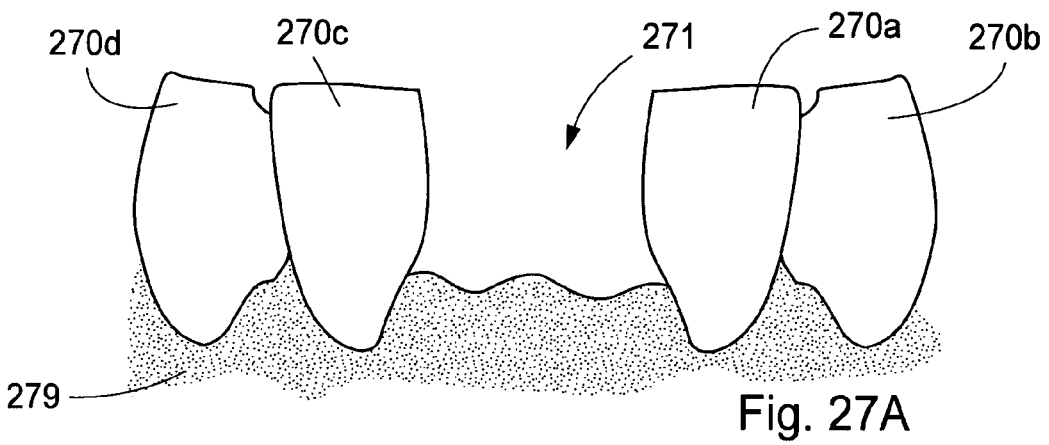
FIGS. 27A-27C are schematic illustrations of a patient jaw missing two teeth, an automatically planned two implant bridge structure, and a manually corrected position of the dental restoration with automatically adapted bridge framework, veneering and implants.
Figure 27B:
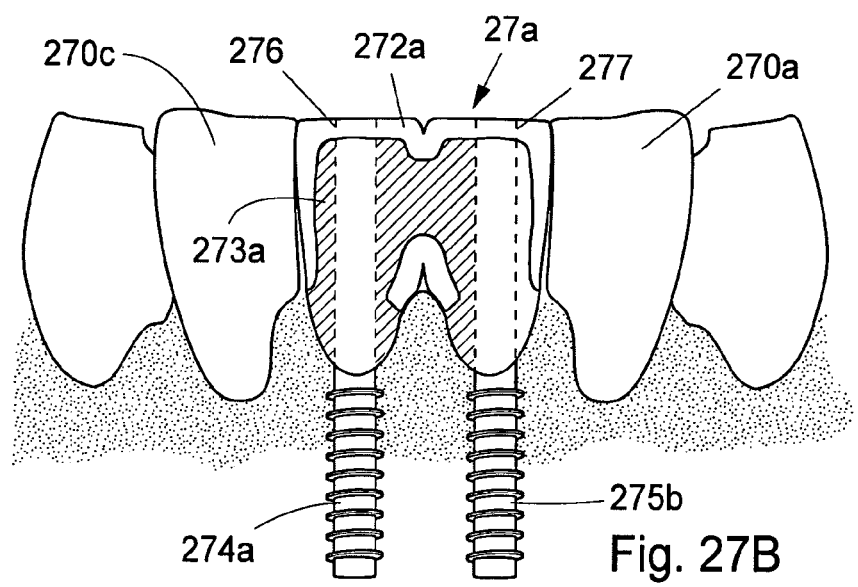
Figure 27C:
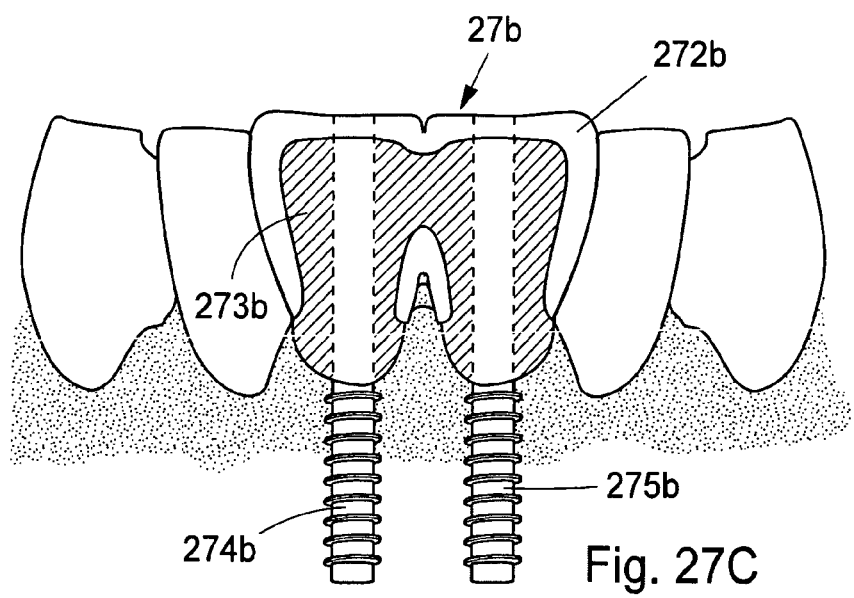

FIGS. 27A-27C are schematic illustrations of a patient missing two teeth. A gap 271 has formed in the dental arch of the patient at the position of the two missing teeth. Remaining are teeth 270a-d. In FIG. 27B a suggestion of an automatically planned dental restoration 27a comprising two implants 274a, 274b, a bridge framework 273a and veneering 272a, is illustrated. The bridge framework 273a and veneering 272a have two bores 276, 277 for installation to dental implants 274a and 275a, respectively. The automatically planned suggestion of dental restoration 27a is based on two template teeth from a teeth library in order to fill the gap 271 along the dental arch of the patient and to fit an occlusion line, as calculated from the remaining teeth in the dental arch, and optionally also from anatomically fixed reference points. Due to the local situation of the patient, or due to esthetical reasons, it might be desired to manually adjust the suggested planning of the dental restoration 27a. This may for instance be due to esthetical reasons. In some embodiments, it may be desired to have larger teeth than the gap 271 allows when automatically interfitting library teeth therein. The result of a manually modified planning is shown in FIG. 27C, showing a modified virtually planned dental restoration 27b comprising adjusted dental implants 274b, 275b, an adjusted bridge framework 273b and veneering 272b. The manually corrected position of the automatically planned and suggested dental restoration 27a may be based on a scaling of the template teeth which are provided by the above mentioned automatically planned suggestion of dental restoration 27a. Alternatively or additionally a manually corrected position may be based on different sized, larger or smaller, template teeth from the teeth library. The adapted bridge framework 273b, veneering 272b and implants 274b, 275b may automatically be chosen, based on the user input of the desired modified position and extension of the adjusted dental restoration 27b. Locked surfaces that are fixed are the outer surface of the adjacent teeth 270a and 270c. When moving the virtual teeth past the occlusion line of the dental arch, automatic planning takes teeth that might be present in the opposed jaw into consideration, such that an occlusion is provided that is comfortable for the patient.

Diagnosis allowing for orthodontic or surgical corrections of the remaining teeth and automatic adaptation of dental restorations to such corrected teeth positions may be provided. Orthodontic or surgical corrections of the remaining teeth may also be made without a dental restoration, based on the automatically calculated positions of teeth from anatomically fixed reference points.

Figure 28:
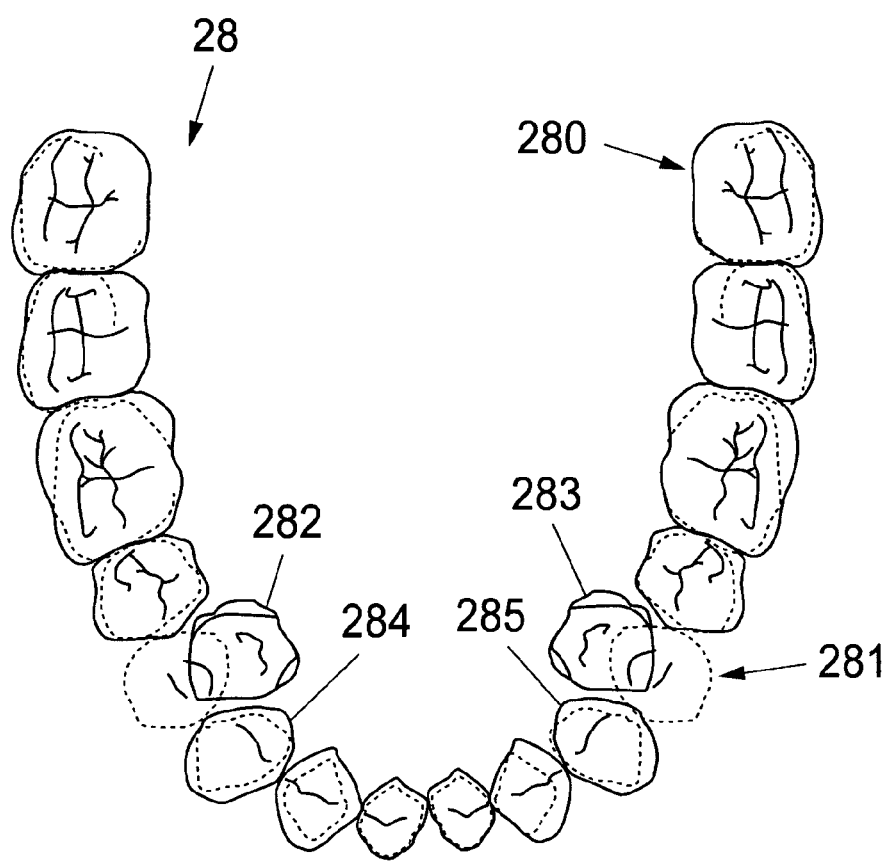
FIG. 28 is a schematic illustration of automatically suggested positions of teeth in relation to anatomically existing teeth of a patient.

FIG. 28 is a schematic illustration of a dental arch 28 of a mandibula of a patient. The anatomically existing teeth 280 are illustrated in continuous lines. Data for the position of these anatomically existing teeth 280 may be provided according to the methods described above, that means for instance medical imaging methods, dental tray impressions converted to 3D data, or intra oral 3D scanning methods. Based on this data, automatically suggested positions of virtually planned teeth 281 in relation to the anatomically existing teeth 280 of the patient may be calculated. The virtually planned teeth 281 are shown in dashed lines. A visualization of this situation on a data monitor of a medical workstation allows for planning of a correction of irregularities of the anatomically existing teeth 280. In the illustrated non-limiting example, two premolar teeth 282, 283, adjacent to the canines 284, 285, deviate substantially from the automatically suggested positions of the virtually planned teeth 281. This deviation may be color encoded for visualization purposes in order to allow for a quick estimation of the patient's dental situation and possibilities for correction thereof. Based on this analysis, a dental correction may be planned. The dental correction may include surgical extraction of existing teeth and/or an orthodontic regulation of the position of certain teeth. A dental restorative procedure may be planned virtually by moving the representation of the anatomically existing teeth 280, guided by the suggested positions of virtually planned teeth 281. The user may lock the position of teeth, e.g., one by one. In case dental restorations are planned for the correction of the dental situation, these may be automatically calculated based on the locked surfaces, e.g., of adjacent teeth and the occlusion. When a desired correction of the dental situation is virtually planned, positions of dental implants, bridge frameworks, veneerings, or copings and crowns may automatically be calculated. The data thus provided may be used for production of the dental restorations and products related thereto, as described above. Manual corrections of the dental restorations may be made before finally accepting the planning by the user.

FIG. 29 is a schematic illustration of a virtually planned dental restoration 29 based on a preparation of an anatomically existing tooth 290 of a patient. The tooth 290, adjacent to two teeth 292, 293, is prepared, as illustrated in the upper illustration of FIG. 29. The tooth 290 is thus provided with a preparation surface 291 for attachment of a dental restoration. Data for virtually planning the dental restoration is provided by e.g., a dental impression that is 3D scanned or an intra oral scanner. In the automatic planning of dental restoration 29 the preparation surface 291 is locked, as well as the surfaces of the adjacent teeth 292, 293. Furthermore, the occlusion line, that may be determined from anatomically fixed reference points as described above or optionally from a bite index, may be locked. Alternatively a virtual articulator may be used to provide a virtually planned dental restoration with an advantageous occlusion. Based on these locked surfaces, the dental restoration is planned. The outer surface of a veneering 295 is determined based on the restraints provided by the locked surfaces. An intermediate coping 294 is automatically calculated from the connection interfaces towards the preparation and the veneering, respectively. The intermediate coping may be optimized by morphing, as explained above. The automatically planned dental restoration 29 may be manually corrected by a user on a medical workstation. Alternatively, the virtually planned dental restoration 29 may be produced directly without user approval. The produced dental restoration may then be affixed to the preparation of tooth 290 according to known methods, e.g., by using dental cement or bonding.

FIG. 30A is a schematic illustration of implantation of a dental implant in jaw bone tissue 308 upon extraction of a tooth 300. Extraction of the tooth 300 leaves a gap 303 between two adjacent teeth 301, 302. Upon extraction of tooth 300, the gap 303 extends into jaw bone tissue 308. By means of a drill guide 304 a bore may be provided at that position in order to implant a dental implant 305. The dental implant may be provided with a healing cap 306 leading to an exact apposition of the surrounding soft tissue with simultaneous shaping of the gingiva upon healing of the extraction site. In the lowermost illustration of FIG. 30A the implant 307 is osseointegrated with new bone tissue 307 that has formed during a subsequent healing phase. Implant 307 is now ready for virtual planning of a complete dental restoration, which will be described below with reference to FIG. 30C.

FIG. 30B is a schematic illustration of implantation of a dental implant 312 in healed jaw bone tissue 314 at the position of a tooth gap 310 between adjacent teeth 315, 316. By means of a drill guide 311, which position may be controlled by the teeth 315, 316 adjacent the gap 310, or supported by the soft tissue, a bore may be provided in order to receive the dental implant 312. Alternatively or additionally the form or topography of the soft tissue may be used for providing data for forming the inside of the drill guide during production. The dental implant 312 may be provided with a healing cap 313. In the lowermost illustration of FIG. 30B the implant 313 is osseointegrated with the bone tissue 314. The implant 307 is now ready for virtual planning of a complete dental restoration.

FIG. 30C is a schematic illustration of virtual planning of a dental restoration taking into consideration a dental implant 320 already existing in the anatomy of a patient. Dental implant 320 is provided in jaw bone tissue 327 of a patient in a gap 321 between adjacent teeth 322, 323. A distance 324 may be arranged on the dental implant 320. Data for the virtual planning of a dental restoration 30 is provided as indicated above, e.g., by a dental impression that is 3D scanned. The top surface of the dental implant 320 or the distance 324 is final and cannot be modified during planning, e.g., it is locked for virtual planning.

Existing anatomical structures, teeth, dental implants or other dental restorations of the craniooral space may be identified for consideration in the automatic planning of a dental restoration by surface identification methods. For instance an existing dental implant may be identified in data from a dental impression by the characteristic shape or dimensions thereof.

Alternatively, density thresholding, e.g., of the acquired Hounsfield value of CT scans, may assist in identifying objects in patient data of the craniooral space. A segmentation into e.g., soft tissue and bone tissue or teeth may be made for modeling such objects. When anatomically existing objects are identified their outer surfaces may be locked for virtual planning of dental restorations. On the other hand, automatic virtual planning takes these locked surfaces into consideration. For instance an outer shape of a dental bridge framework at the connection interface to a dental implant may automatically be shaped to match the corresponding locked top surface of the dental implant. Alternatively, a top surface of the dental bridge framework may automatically be shaped to match the corresponding inner surface of a veneering when the top surface of the reconstructed tooth also is determined to be at a final spatial position.

Returning to FIG. 30C, the dental restoration 30 is automatically virtually planned to fit onto the top surface of the dental implant 320 or the distance attached thereto. An outer shape of a reconstructed tooth, here of a crown 326 is determined with relation to the existing adjacent teeth 322, 323 and a desired occlusion, e.g., a topmost coronal position of the crown 326. Based on these constraints, a coping is automatically shaped to matchingly fit between the inner surface of the crown and the top surface of the dental implant 320 or distance 324. The connection interface at the inner surface of the crown 326 may be designed such that structural strength requirements of the dental restoration 30 are fulfilled advantageously.

In summary, a semi-finished product or a finished product may be provided based on data from the automatic planning method described above. Dynamical modifications may be made during the virtual planning, whereby anatomically existing teeth or dental restorations are considered. A semi-finished product is for instance a dental implant and an associated dental bridge framework, for which a dental technician may manually produce the final veneering of the dental restoration. When providing a finished product, even the veneering may be provided automatically. Furthermore the necessary tools for inserting the virtually planned and produced dental restorations may be produced. For instance, a surgical template for drilling bores, as well as the corresponding drills may be produced.

Figure 31:
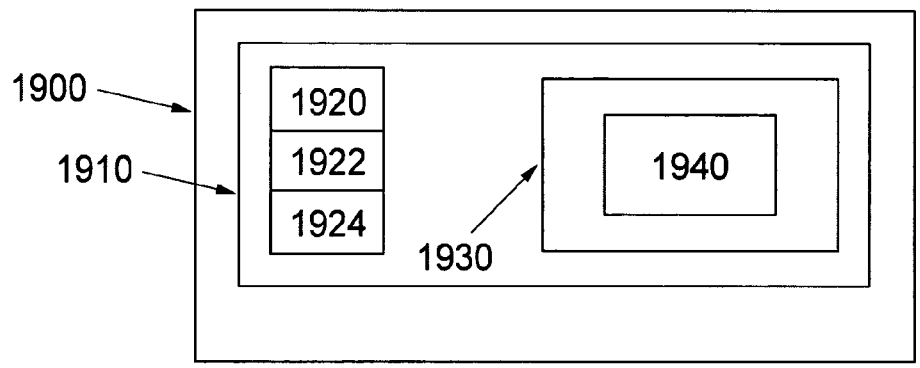
FIG. 31 is a schematic illustration of an example embodiment of a system of the invention.
Figure 32:
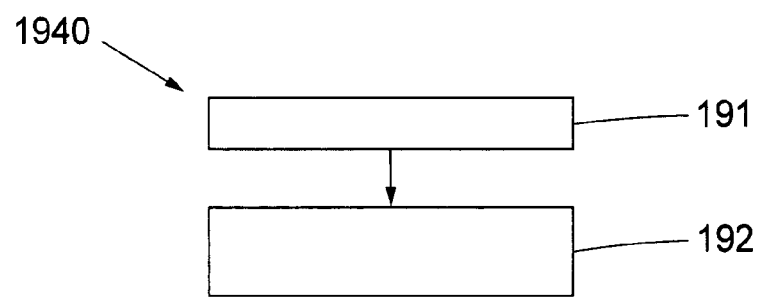
FIG. 32 is a schematic illustration of a computer readable medium having embodied thereon a computer program according to an embodiment of the invention.

An embodiment for a system for performing the above described method is schematically illustrated in FIG. 31.

The system 1900 provides computer-based planning of a dental restorative procedure of a patient having a craniooral space, and/or of at least one dental component for said dental restorative procedure. The system 1900 has a first unit 1922 for determining a first spatial position of a first boundary surface, in said craniooral space, of a first dental unit of a dental restoration; a second unit 1924 for determining a second spatial position of a second boundary surface, in said craniooral space remote said first boundary surface, of a second dental unit of said dental restoration; and a third unit for determining a third spatial position, of at least a portion of said dental component, relative at least one of said first and second spatial positions.

A medical workstation 1910 comprises the usual computer components like a central processing unit (CPU) 1920, memory, interfaces, etc. Moreover, it is equipped with appropriate software for processing data received from data input sources, such as data obtained from CT scanning or 3D scanning. The software may for instance be stored on a computer readable medium 1930 accessible by the medical workstation 1910. The computer readable medium 1930 may comprise the software in form of a computer program 1940 comprising suitable code segments 190, 191, for planning a dental restorative procedure of a patient and for planning dental components related to the dental restorative procedure. The medical workstation 1910 further comprises a monitor, for instance for the display of rendered visualizations, as well as suitable human interface devices, like a keyboard, mouse, etc., e.g., for manually fine tuning the automatic planning otherwise provided by the software. The medical workstation may be part of a system 1900 for planning a dental restorative procedure of a patient and for planning dental components related thereto. The medical workstation may also provide data for producing at least one of a dental restoration and a product related to the dental restorative procedure.

For planning, patient data, e.g., from a CT scan, is imported into a software for pre-surgical planning of dental restorative procedures, for instance run on the medical workstation 1910. The medical workstation 1910 may have a graphical user interface for computer-based planning of a dental restorative procedure of a patient having a craniooral space, and/or of at least one dental component for said dental restorative procedure. The graphical user interface may comprise components for visualizing the method described above in this specification or recited in the attached claims.

When the pre-surgical planning is made, production of dental restorations and/or products related to said pre-surgical planning, such as surgical templates, may be made. In an embodiment the computer program 1940 is useful for computer-based planning of a dental restorative procedure of a patient having a craniooral space, and/or of at least one dental component for said dental restorative procedure, such as a bridge framework, veneering, surgical template etc. The computer program comprises a first code segment 190 for determining a first spatial position of a first boundary surface, in the craniooral space of the patient, of a first dental unit, e.g., a veneering, bridge framework or dental implant, of a dental restoration. A second code segment 191 is provided for determining a second spatial position of a second boundary surface, which is positioned remote the first boundary surface, of a second dental unit of the dental restoration. The second dental unit is different from said first dental unit and may comprise a veneering, bridge framework or dental implant. The computer program may further comprise a third code segment for determining a third spatial position, of at least a portion of the dental component, relative at least one of the first and second spatial positions. The dental component may for instance be the veneering, bridge framework or dental implant, or a surgical template. For instance, the first spatial position is that of the top surface of a tooth at an occlusion line, the second spatial position is that of a top surface of a dental implant and the third spatial position is that of the connection interface between a bridge framework and the veneering. The computer program may enable carrying out of the method described above in this specification or recited in the attached claims. The computer program may be embodied on a computer readable medium. As mentioned above, the computer program may be executed on a medical workstation or similar computing apparatus suitable for virtual calculations and design purposes.

As used herein, the singular forms "a", "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

As will be appreciated by one of skill in the art, certain embodiments of the present invention may be embodied as a device, system, method or computer program product. Accordingly, certain embodiments of the present invention may take the form of an entirely hardware embodiment, a software embodiment, or an embodiment combining software and hardware aspects.

Furthermore, certain embodiments of the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Embodiments of the present invention are described herein with reference to flowchart and/or block diagrams. It will be understood that some or all of the illustrated blocks may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

It is to be understood that the functions/acts noted in the diagrams may occur out of the order noted in the operational illustrations. For example, two blocks shown in succession may in fact be executed substantially concurrently or the blocks may sometimes be executed in the reverse order, depending upon the functionality/acts involved. Although some of the diagrams include arrows on communication paths to show a primary direction of communication, it is to be understood that communication may occur in the opposite direction to the depicted arrows. The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

What is claimed is:

1. A method for computer-based planning of a dental restorative procedure for a patient having a craniooral space and for computer-based planning of a bridge framework for said dental restorative procedure, said method comprising:
   determining a first spatial position of a first boundary surface, in said craniooral space, of a veneering of a dental restoration by identifying at least one anatomically fixed reference point that is anatomically stable in a craniooral data set acquired from said patient and then determining from said at least one anatomically fixed referenced point a position in space of at least one of a virtual tooth or an occlusion line, said first boundary surface to be arranged coronally at said occlusion line of said patient;
   determining a second spatial position of a second boundary surface, in said craniooral space remote said first boundary surface, of a dental implant of said dental restoration, wherein a top surface of said dental implant is said second boundary surface; and
   determining via a computer a third spatial position of at least a portion of said bridge framework relative to at least one of said first and second spatial positions.

2. The method according to claim 1, comprising determining at least one of said first and second spatial positions as a final spatial position thereof.

3. The method according to claim 1, comprising adjusting said third spatial position in dependence of an adjustment of at least one of said first and second spatial positions.

4. The method according to claim 1, wherein said bridge framework has a first outer surface to be arranged apically at a first connection interface, and a second outer surface to be arranged coronally at a second connection interface.

5. The method according to claim 4, comprising:
   determining said second spatial position as a final spatial position thereof;
   establishing said first connection interface as a final first connection interface;
   determining said third spatial position relative said final first connection interface; and
   establishing said second connection interface as a final second connection interface.

6. The method according to claim 4, wherein said veneering has a second outer surface to be arranged at said second connection interface, and wherein said dental implant has a first outer surface oriented coronally at said first connection interface.

7. The method according to claim 6, comprising:
   determining a position and an angulation of said dental implant; and
   establishing said first connection interface as a final first connection interface.

8. The method according to claim 6, comprising determining said third spatial position of said second outer surface of said bridge framework relative said first spatial position of said first boundary surface and thereby establishing said second connection interface as a final second connection interface.

9. The method according to claim 1, comprising:
   manually fine tuning a position of said dental implant or said veneering; and
   automatically adapting the corresponding connection interfaces of the remaining dental units of the dental restoration.

10. The method according to claim 1, further comprising:
identifying at least three anatomically fixed reference points that are anatomically stable in a craniooral data set acquired from said patient; and
determining a position in space of at least one tooth having one of said first spatial position and second spatial position from said anatomically fixed reference points.

11. The method according to claim 1, comprising determining said third spatial position by a morphing technique.

12. The method according to claim 1, further comprising producing a bridge framework based on data obtained from said determined spatial positions.

13. The method according to claim 1, further comprising producing a dental veneering based on data obtained from said determined spatial positions.

14. The method according to claim 1, further comprising:
producing a bridge structure comprising a bridge framework and a veneering based on data obtained from said determined spatial positions; and
attaching said veneering to said bridge framework.

15. The method according to claim 1, further comprising producing a surgical template comprising at least one drill guide based on data obtained from said determined spatial positions.

16. The method according to claim 1, comprising automatically adapting a shape of a bridge framework, the shape of a dental veneering, and the position of a dental implant.

17. A system for computer-based planning of a dental restorative procedure of a patient having a craniooral space and for computer-based planning a bridge framework for said dental restorative procedure, said system comprising:
a first unit configured to determine a first spatial position of a first boundary surface, in said craniooral space, of a veneering of a dental restoration, by identifying at least one anatomically fixed reference point that is anatomically stable in a craniooral data set acquired from said patient and then determining from said at least one anatomically fixed referenced point a position in space of at least one of a virtual tooth or an occlusion line, said first boundary surface to be arranged coronally at an occlusion line of said patient;
a second unit configured to determine a second spatial position of a second boundary surface, in said craniooral space remote said first boundary surface, of a dental implant of said dental restoration, wherein a top surface of said dental implant is said second boundary surface; and
a third unit configured to determine a third spatial position of at least a portion of said bridge framework relative to at least one of said first and second spatial positions.

18. A computer readable medium having embodied thereon in a non-transitory manner a computer program for computer-based planning of a dental restorative procedure of a patient having a craniooral space and for computer-based planning a bridge framework for said dental restorative procedure, said computer program comprising:
a first code segment configured to determine a first spatial position of a first boundary surface, in said craniooral space, of a veneering of a dental restoration, by identifying at least one anatomically fixed reference point that is anatomically stable in a craniooral data set acquired from said patient and then determining from said at least one anatomically fixed referenced point a position in space of at least one of a virtual tooth or an occlusion line, said first boundary surface to be arranged coronally at an occlusion line of said patient;
a second code segment configured to determine a second spatial position of a second boundary surface, in said craniooral space remote said first boundary surface, of a dental implant of said dental restoration, wherein a top surface of said dental implant is said second boundary surface; and
a third code segment configured to determine a third spatial position of at least a portion of said bridge framework relative to at least one of said first and second spatial positions.

19. A medical workstation configured to carry out the method of claim 1.

* * * * *